US009983134B2

(12) United States Patent
Ragan

(10) Patent No.: US 9,983,134 B2
(45) Date of Patent: *May 29, 2018

(54) SYSTEMS AND METHODS FOR IMAGING AND PROCESSING TISSUE

(71) Applicant: Timothy Ragan, Somerville, MA (US)

(72) Inventor: Timothy Ragan, Somerville, MA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 14/300,425

(22) Filed: Jun. 10, 2014

(65) Prior Publication Data

US 2014/0356876 A1 Dec. 4, 2014

Related U.S. Application Data

(63) Continuation of application No. 13/297,035, filed on Nov. 15, 2011, now Pat. No. 8,771,978.

(60) Provisional application No. 61/413,543, filed on Nov. 15, 2010.

(51) Int. Cl.
G01N 21/64 (2006.01)
G01N 1/06 (2006.01)
G02B 21/00 (2006.01)
G02B 21/36 (2006.01)
A61B 3/10 (2006.01)
G01B 9/02 (2006.01)
C12Q 1/68 (2018.01)
G01N 1/30 (2006.01)
G01N 33/53 (2006.01)
G01N 21/65 (2006.01)

(52) U.S. Cl.
CPC ......... *G01N 21/6458* (2013.01); *A61B 3/102* (2013.01); *C12Q 1/686* (2013.01); *G01B 9/02091* (2013.01); *G01N 1/06* (2013.01); *G01N 1/30* (2013.01); *G01N 33/53* (2013.01); *G02B 21/008* (2013.01); *G02B 21/367* (2013.01); *G01N 2001/068* (2013.01); *G01N 2021/653* (2013.01); *G01N 2223/40* (2013.01); *G01N 2223/401* (2013.01); *G01N 2223/419* (2013.01)

(58) Field of Classification Search
CPC .... G01N 1/06; G01N 21/6458; G02B 21/008; A61B 3/102
See application file for complete search history.

(56) References Cited

U.S. PATENT DOCUMENTS

| 4,960,330 | A | 10/1990 | Kerschmann |
| 5,139,338 | A | 8/1992 | Pomerantz et al. |
| 7,372,985 | B2* | 5/2008 | So ..................... G06K 9/00127 382/133 |
| 7,724,937 | B2 | 5/2010 | So et al. |
| 7,772,985 | B2 | 8/2010 | Kobayashi et al. |
| 8,238,632 | B2 | 8/2012 | Wilson et al. |
| 8,384,907 | B2 | 2/2013 | Tearney et al. |
| 8,771,978 | B2 | 7/2014 | Ragan |
| 2006/0014287 | A1* | 1/2006 | Sherwood ............ C12N 5/0659 435/455 |
| 2006/0158655 | A1 | 7/2006 | Everett et al. |
| 2006/0179992 | A1 | 8/2006 | Kermani |
| 2007/0038121 | A1 | 2/2007 | Feldman et al. |
| 2007/0057211 | A1 | 3/2007 | Bahlman et al. |
| 2007/0091428 | A1 | 4/2007 | Wilson et al. |
| 2007/0229801 | A1 | 10/2007 | Tearney et al. |
| 2007/0258122 | A1* | 11/2007 | Champoulov ..... G02B 21/0036 702/1 |
| 2007/0260138 | A1 | 11/2007 | Feldman et al. |
| 2008/0154128 | A1 | 6/2008 | Milner |
| 2009/0091566 | A1 | 4/2009 | Turney et al. |
| 2009/0093709 | A1 | 4/2009 | Patel et al. |
| 2010/0000383 | A1 | 1/2010 | Koos et al. |
| 2010/0081190 | A1 | 4/2010 | Hyde et al. |
| 2010/0081915 | A1 | 4/2010 | Hyde et al. |
| 2010/0093022 | A1 | 4/2010 | Hayworth et al. |

(Continued)

FOREIGN PATENT DOCUMENTS

WO 2006/127967 A2 11/2006
WO 2006/135769 A1 12/2006

(Continued)

OTHER PUBLICATIONS

Hillman et al, Depth-resolved optical imaging and microscopy of vascular compartment dynamics during somatosensory stimulation, 2007, NeuroImage, 35, 89-104.*
Allen, Bringing Clarity to the study of the brain. Retrieved online at: http://membercentral.aaas.org/blogs/qualia/bringing-clarity-study-brain. 3 pages. Mar. 11, 2013.
Augustinack et al., MRI parcellation of ex vivo medial temporal lobe. NeuroImage. Article in Press, 2013, 8 pages.
Chasles et al., Optimization and characterization of a structured illumination microscope. Opt Express. Nov. 26, 2007;15(24):16130-40.

(Continued)

*Primary Examiner* — Narayan Bhat
(74) *Attorney, Agent, or Firm* — McCarter & English, LLP

(57) ABSTRACT

In accordance with preferred embodiments of the present invention, a method for imaging tissue, for example, includes the steps of mounting the tissue on a computer controlled stage of a microscope, determining volumetric imaging parameters, directing at least two photons into a region of interest, scanning the region of interest across a portion of the tissue, imaging a plurality of layers of the tissue in a plurality of volumes of the tissue in the region of interest, sectioning the portion of the tissue, capturing the sectioned tissue, and imaging a second plurality of layers of the tissue in a second plurality of volumes of the tissue in the region of interest, and capturing each sectioned tissue, detecting a fluorescence image of the tissue due to said excitation light; and processing three-dimensional data that is collected to create a three-dimensional image of the region of interest. Further, captured tissue sections can be processed, re-imaged, and indexed to their original location in the three dimensional image.

27 Claims, 21 Drawing Sheets

(56) References Cited

U.S. PATENT DOCUMENTS

| | | | |
|---|---|---|---|
| 2010/0323445 A1 | 12/2010 | Hayworth et al. |
| 2011/0058178 A1 | 3/2011 | Tearney et al. |
| 2011/0320174 A1 | 12/2011 | Ragan et al. |
| 2012/0208184 A1 | 8/2012 | Ragan |
| 2013/0010283 A1 | 1/2013 | Villiger et al. |
| 2013/0149734 A1 | 6/2013 | Ammar et al. |

FOREIGN PATENT DOCUMENTS

| | | |
|---|---|---|
| WO | 2007/149971 A2 | 12/2007 |
| WO | 2010/045400 A3 | 7/2010 |
| WO | 2011/163484 A2 | 12/2011 |
| WO | 2012/068142 A2 | 5/2012 |

OTHER PUBLICATIONS

Dubois et al., High-resolution full-field optical coherence tomography with a Linnik microscope. Appl Opt. Feb. 1, 2002;41(4):805-12.

Goldman, Lightning strikes twice: Optogenetics pioneer Karl Deisseroth's newest technique renders tissues transparent, yet structurally intact. Scope, Stanford Medicine. Retrieved online at: http://scopeblog.stanford.edu/2013/04/10/lightning-strikes-twice-optogenetics-pioneer-karl-deisseroths-newest-technique-renders-tissues-transparent-yet-structurally-intact/ 2 pages. Apr. 10, 2013.

Jeong et al., Combined two-photon microscopy and optical coherence tomography using individually optimized sources. Opt Express. Jul. 4, 2011;19(14):13089-96.

Lim et al., Wide-field fluorescence sectioning with hybrid speckle and uniform-illumination microscopy. Opt Lett. Aug. 15, 2008;33(16):1819-21.

Makhlouf et al., A dual modality fluorescence confocal and optical coherence tomography microendoscope. Endoscopic Microscopy V. Guillermo J. Tearney (Ed.), Proceedings of SPIE BiOS. Feb. 24, 2010;7558:75580K-1-75580K-8.

Osten, CSHL team introduces automated imaging to greatly speed whole-brain mapping efforts. Cold Spring Harbor, N.Y. 4 pages, Jan. 12, 2012.

Ragan et al., Serial two-photon tomography: an automated method for ex-vivo mouse brain imaging. Nat Methods. Sep. 1, 2012;9(3):255-258.

Tang et al., Combined multiphoton microscopy and optical coherence tomography using a 12-fs broadband source. J Biomed Opt Mar.-Apr. 2006;11(2):020502. 3 pages.

Wang et al., Reconstructing micrometer-scale fiber pathways in the brain: multi-contrast optical coherence tomography based tractography. Neuroimage. Oct. 15, 2011;58(4):984-92.

International Search Report for Application No. PCT/US2011/060831, dated Jul. 17, 2012. 7 pages.

International Search Report for Application No. PCT/EP2011/066246, dated Jan. 23, 2012. 5 pages.

International Preliminary Report on Patentability for Application No. PCT/EP2011/066246, dated Mar. 28, 2013. 10 pages.

* cited by examiner

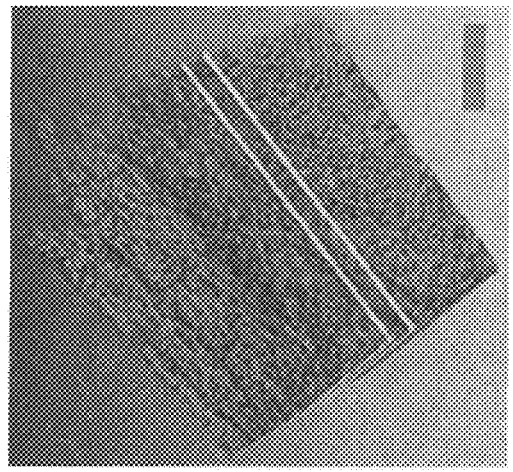
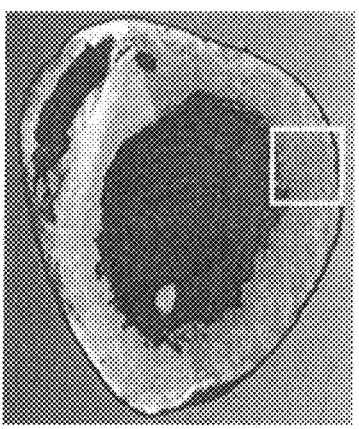
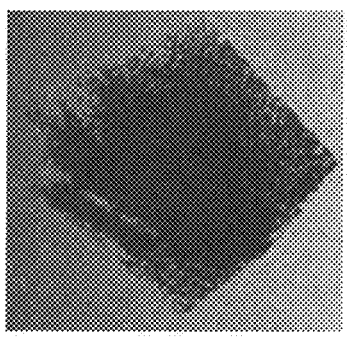
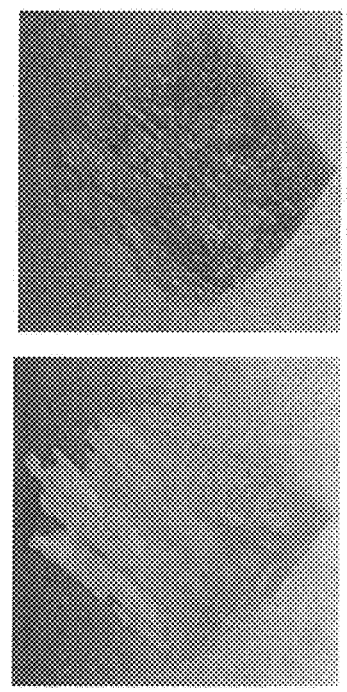
FIG. 1A  FIG. 1B  FIG. 1C  FIG. 1D  FIG. 1E

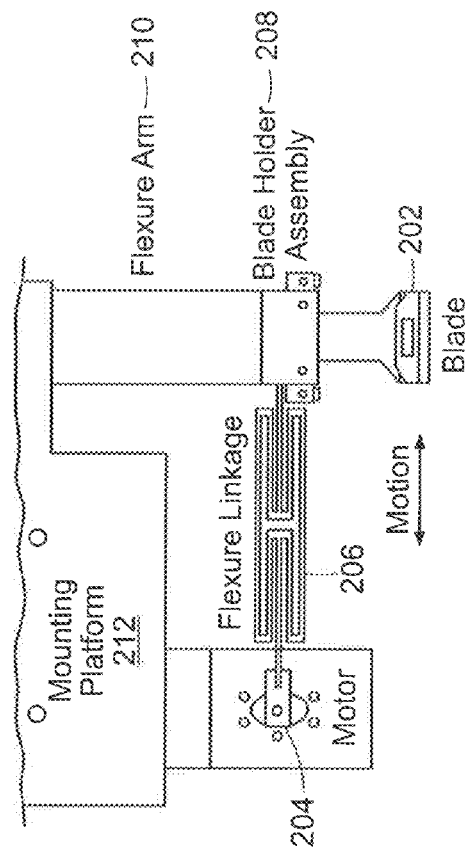
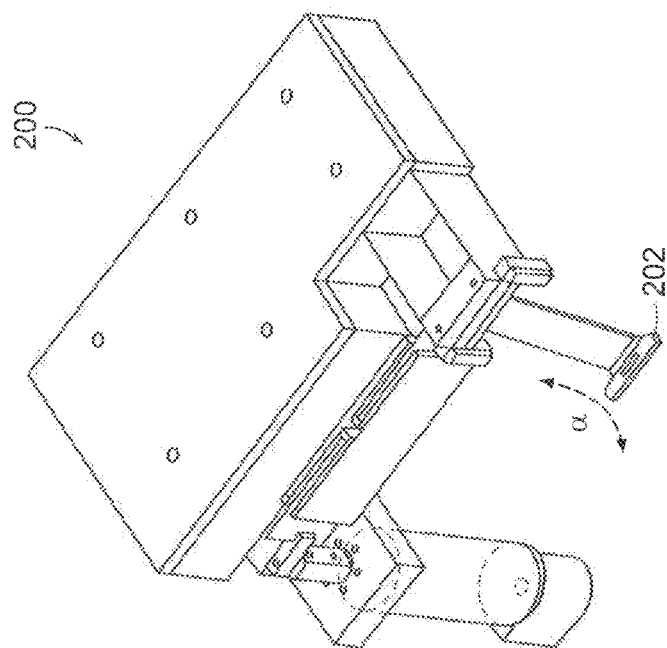
FIG. 4B
FIG. 4A

F = Frequency
A = Amplitude

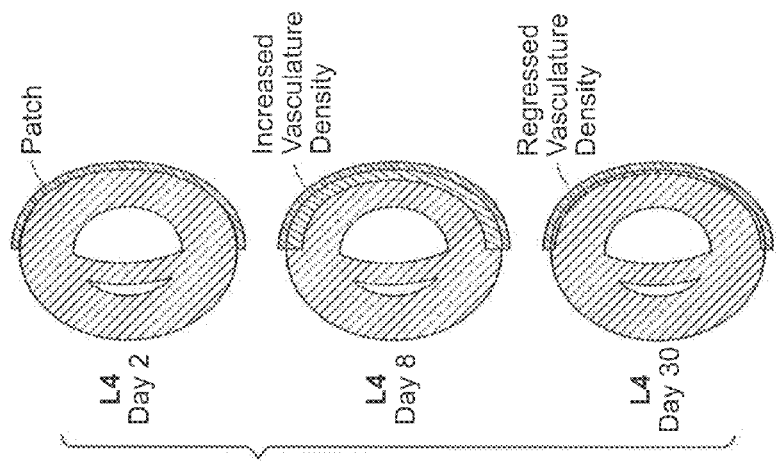
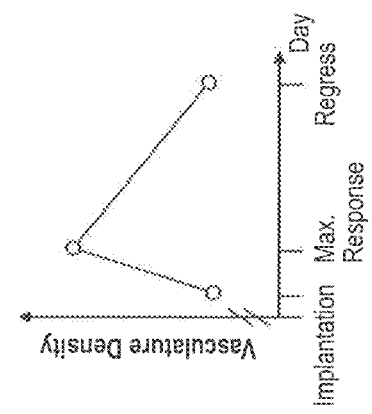
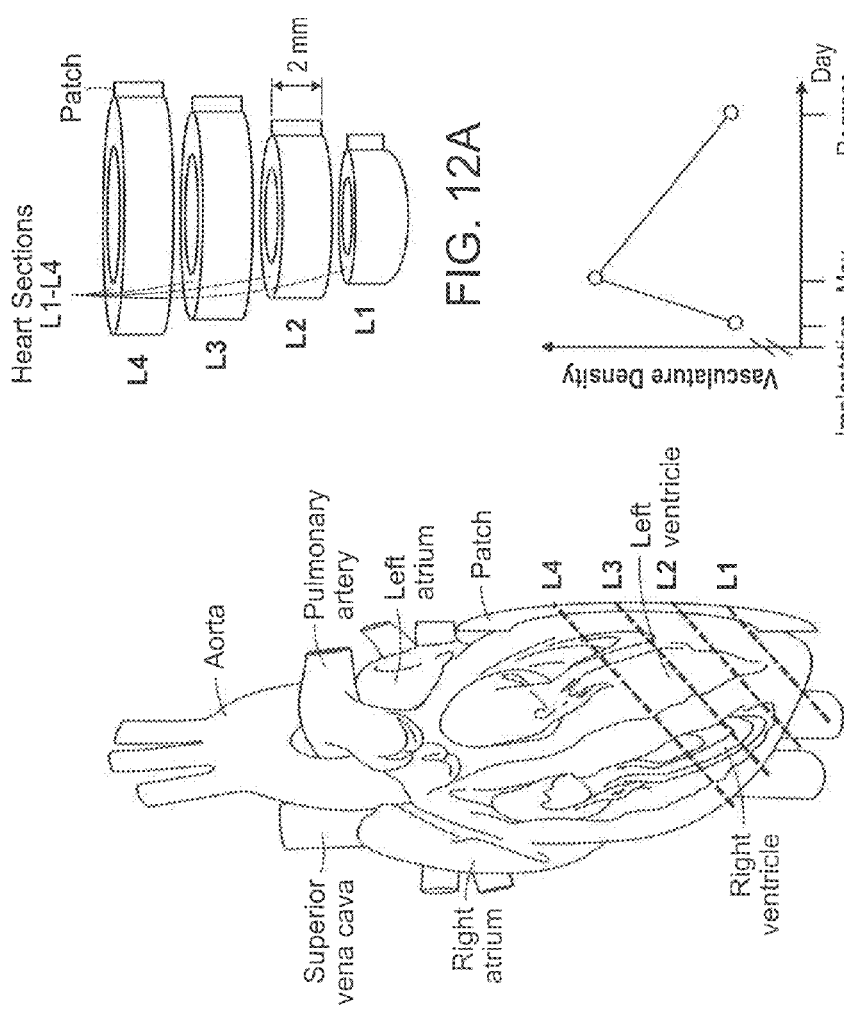
FIG. 12C
FIG. 12A
FIG. 12B
FIG. 11

Whole Brain Atlas

Adjustable Resolution

YFP lageled neurons, taken with a 16x Nikon, 0.8NA, λ=900nm

SYSTEMS AND METHODS FOR IMAGING AND PROCESSING TISSUE

CROSS REFERENCE TO RELATED APPLICATION

This application is a continuation application of U.S. application Ser. No. 13/297,035 filed Nov. 15, 2011 which claims priority to U.S. Provisional Application No. 61/413,543, filed Nov. 15, 2010, the entire contents of the above applications being incorporated herein by reference.

BACKGROUND OF THE INVENTION

This invention addresses the pressing need in biomedical science for imaging and tissue processing methods which can quickly image multiple components in thick tissues and whole organs with high molecular specificity. In order to develop methods which achieve this goal, the choice of an appropriate imaging technology is critical. Important criteria include spatial resolution, sensitivity, depth penetration, molecular specificity, data throughput and compatibility with the many biochemical methods such as immunohistochemistry or FISH analysis. Many methods to image 3D thick tissues have been developed, but most of these techniques do not have subcellular resolution or the necessary molecular sensitivity. For instance, while high resolution MRI is capable of imaging whole animals, its resolution is limited to 10-100 µm and is not compatible with common fluorescent markers. In comparison, optical imaging methods in general provide the highest resolution and specificity. Optical coherence tomography has a few-micron level resolution and a penetration depth of a few millimeters, however, optical coherence tomography does not provide reliable subcellular level imaging today. Optical projection tomography is more compatible with molecular imaging and can study fluorescent and non fluorescently stained tissues up to approximately 15 mm. However it also does not possess sufficient resolution to resolve details of individual cells and has difficulty in imaging tissues containing opaque materials such as bone or cartilage. Sheet plane illumination techniques, such as selective plane illumination microscopy (SPIM) has demonstrated the ability to provide detailed images of over a millimeter of relatively transparent samples such as embryos but, due to the residual scattering that exists even in optically cleared samples, SPIM and similar techniques have limitations with opaque samples and with samples which have an extent over several millimeters or which possess weak fluorescent signals. Further, since it is not generally possible to immunostain whole organs due to the limited diffusivity of antibodies and even of small molecules into intact tissues, sheet plane techniques are of limited use without first sectioning the tissue to allow the penetration of the appropriate labels. This restricts their use in answering many biological questions which require either IHC or FISH analysis to reveal relevant biomarkers.

Among 3D tissue optical imaging techniques, two-photon microscopy (TPM) is particularly promising. TPM is a fluorescent optical microscopy technique. It features sub-micron resolution, low photo-toxicity, excellent penetration depth, and 3D sectioning capability. The excellent depth penetration of TPM in tissues is due to lower scattering and absorption of the infrared excitation wavelength employed and the lack of the need for a detection pinhole allowing greater signal collection efficiency than in confocal microscopy. In addition, like all fluorescence based techniques, it provides high molecular specificity in mapping gene and protein expression profiles, and has clearly demonstrated its utility for visualizing gene activity in vivo with GFP over the past decade.

While, two-photon microscopy (TPM) can image in highly scattering media, it is still limited to approximately less than a millimeter penetration into opaque samples. To overcome the depth penetration limitation of two-photon microscopy in studying thicker specimens, preferred embodiments of the inventions use an automated microtome integrated into a high speed TPM system. By alternating and overlapping optical sectioning with mechanical sectioning, it is possible to rapidly image samples with arbitrary thickness. Once the upper portion of the sample is imaged, the uppermost portion of the tissue sample can be removed by the microtome. A critical problem with mechanically sectioned tissues, however, is the difficulty in comparative analysis due to stretching, compressing and/or rotation of tissue structures caused by mechanical sectioning. Prior methods have used fiducial markers formed by drilling holes or otherwise altering the tissue to aid in alignment.

While direct intravital tissue labeling, transgenic animals, native tissue autofluorescence, and SHG contrast provide powerful means to visualize the complex 3D biochemical environment within a tissue, there are still a large number of biochemical states and signatures which are only possible to examine by other means, such as immunohistochemistry (IHC) staining. Unfortunately it is very difficult or impossible to reliably IHC stain whole mount tissues greater than approximately 100 microns in depth. This is due to the large size of antibodies used in IHC staining and their subsequent slow diffusion and steric hindrance within the tissue.

SUMMARY OF THE INVENTION

The present invention relates to systems and methods of acquiring a three dimensional image of a tissue sample formed from a plurality of images tissue layers, processing sections of the imaged tissue sample followed by imaging of the processed sections to form a second three dimensional image of the sample and analysis of the first image and second image to characterize the tissue sample.

The present invention relates to systems and methods including moving the optical system, the stage moving, or the vibratome moving for generating images of whole organs or thick tissues. The system can include a transfer system to move tissue sections for storage and registration as well as for further processing and imaging.

Despite the strengths of traditional TPM, it cannot be directly applied to organ level imaging due to three factors. First, the depth penetration of TPM is still limited to a few hundred microns for most tissue types, presenting a barrier to imaging tissue or organs which have a substantive axial extent. Second, the typical field of view of standard TPM has a linear dimension of only a few hundred microns, thus requiring a scanning procedure over an extended period that is impracticable for whole organ imaging. Third, standard TPM systems have an image acquisition speed that is also prohibitively slow for imaging macroscopic 3D tissues. A typical TPM system would require approximately 60 days at a minimum to image a 5 mm cube of tissue at a resolution of 1 cubic µm and 10 µs pixel residence time, for example. Therefore there exists a great benefit to save the sections after they have been removed from the whole mount tissue for further biochemical analysis. Further examples of analysis, but not limited to, are, FISH, mass spectrometry, imaging mass spectrometry, PCR, micro dissection. Afterwards, this additional information can be used independently or combined with the original 3D image which was obtained to extract further biological information from the sample.

Preferred embodiments of the invention can include two-photon 3D tissue image cytometer (or alternatively referred to as a whole mount tissue scanner) using multi-photon excitation. To overcome the depth penetration limitation of two-photon microscopy in studying thicker specimens, preferred embodiments of the inventions use an automated microtome integrated into a high speed TPM system. By alternating and overlapping optical sectioning with mechanical sectioning, it is possible to rapidly image samples with arbitrary thickness. Once the upper portion of the sample is imaged, the uppermost portion of the tissue sample can be removed by the microtome. The depth of mechanical sectioning is chosen to be less than the imaged depth ensuring that the region of the sample that is subjected to mechanical sectioning has been already imaged.

An advantage of this methodology over block face techniques is that any distortions that are introduced by the sectioning procedure do not introduce artifacts in the reconstructed 3D volume since the cut plane is always pre-imaged. Further, imaging of overlapping regions between successive sections ensures accurate digital registration between sections on a pixel by pixel basis. To overcome the limitations in data acquisition speed, two methods of high speed two-photon microscopy can be utilized. To overcome the field of view limitations of the objective, the robotic stage raster scans the sample allowing a larger image to be constructed from a series of overlapping 3D volumes. After the section is removed with the microtoming procedure, the entire sample is translated towards the objective. Unlike with serial section reconstruction, where alignment of successive z-sections is often ambiguous, the integrated precision robotic stage insures high reliability in registering neighboring volumes both in the axial and radial direction. The microscope system is entirely automated and requires no user intervention once the sample has been mounted.

The present invention enables comparative analysis of image data using images obtained both before and after sectioning. Thus, for example, a transgenic mouse engineered to express GFP in a cell if protein X is being expressed can be section, processed and imaged using IHC staining to determine if protein Y is also being expressed. Thus, a particular cell can be determined to have two different biomarker characteristics based on different processing and imaging of the tissue sample.

BRIEF DESCRIPTION OF THE DRAWINGS

FIG. 1A-1G illustrate image data generated by systems and methods of the present invention.

FIGS. 4A-4B illustrate perspective and taps views of a sectioning tool in accordance with the invention.

FIG. 11 illustrate a sectioning sequence of a heart.

FIG. 12A-12C illustrate section analysis of an animal heart.

FIG. 17A-17D illustrate use of adjustable resolution in image processing.

DETAILED DESCRIPTION OF THE INVENTION

Figure 1F:
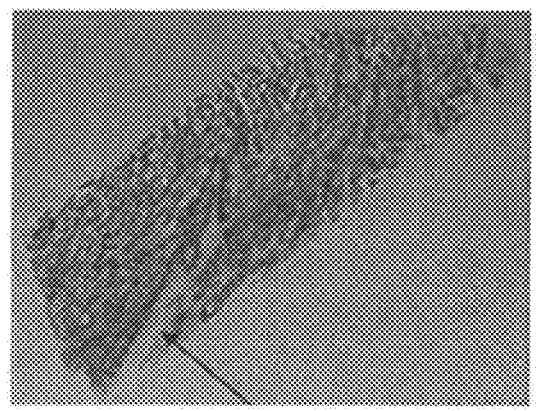
Figure 1G:
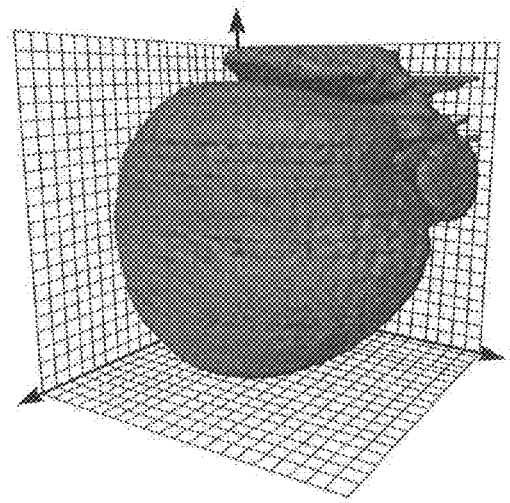

FIG. 1A-1G illustrates image data that can be acquired and processed in accordance with the invention. An entire mouse heart was imaged with sub micron resolution and multispectral detection as shown in FIG. 1A. This system visualizes details at the subcellular level throughout the entire heart, revealing features of the nuclei, vessel architecture, mesoscale architecture such as cleavage planes in the heart, and the macroscopic morphology of the heart chambers. This entire 3D data can span almost five orders of magnitude. FIG. 1B shows autofluorescence of heart tissue with labeled nuclei and vasculature wherein the scale bar is 100 µm. FIG. 1C shows cleavage planes of laminar sheets of sectional myocardium. FIG. 1D shows morphology of the 3D microvasculature. FIG. 1E shows nuclei from the myocytes, fibroblasts and endothelial cells lining the vasculature. FIG. 1F shows the section outlined in FIG. 1B where the arrow indicates space between successive cleavage planes. FIG. 1G shows a whole organ 3D image of a heart that can be imaged after processing as set forth in preferred embodiments of the invention.

Figure 1H:
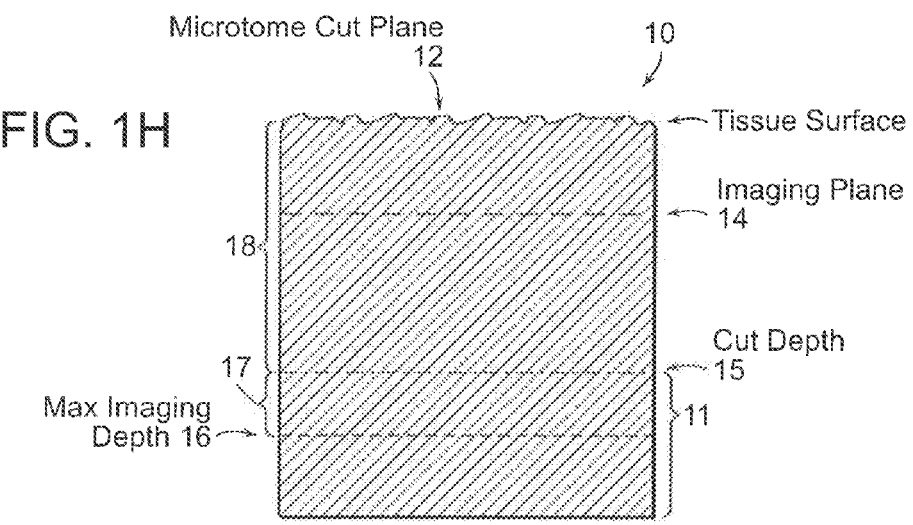
FIG. 1H illustrates the imaging and cutting depths of a sample being imaged in accordance with the invention.

FIG. 1H demonstrates the relation of the imaging plane 14 with respect to the tissue surface 10, surface cut plane 12, and maximum imaging depth 16 in each imaged region (17, 18) of tissue. Imaging below the cut depth in the second region 11 enables more precise registration in the formation of 3D images of whole organs or deep tissue samples as the overlapping region 17 extends below the cut depth 15. This enables registration of the first image region (17 and 18) with the second region 11 which also includes overlap region 17.

FIGS. 2A-2F show systems used for multiphoton multi-focal microscope (MMM). This system can image at over 600 frames per second and significantly deeper into tissues than prior systems. The system performs multispectral detection methods that have better sensitivity and throughput than existing multispectral imaging systems.

A traditional confocal or two-photon system requires approximately 60 days to image an entire mouse heart at sub-micron resolution. However given the high speed imaging employed using the present system, the present system images this in 3.5 days and preferably in approximately 2-5 hours. As and additional example, this system routinely generates mouse brain atlases with 100 micron spacing of coronal sections at 1.4 µm pixel sampling in approximately 4 hours.

Figure 2A:
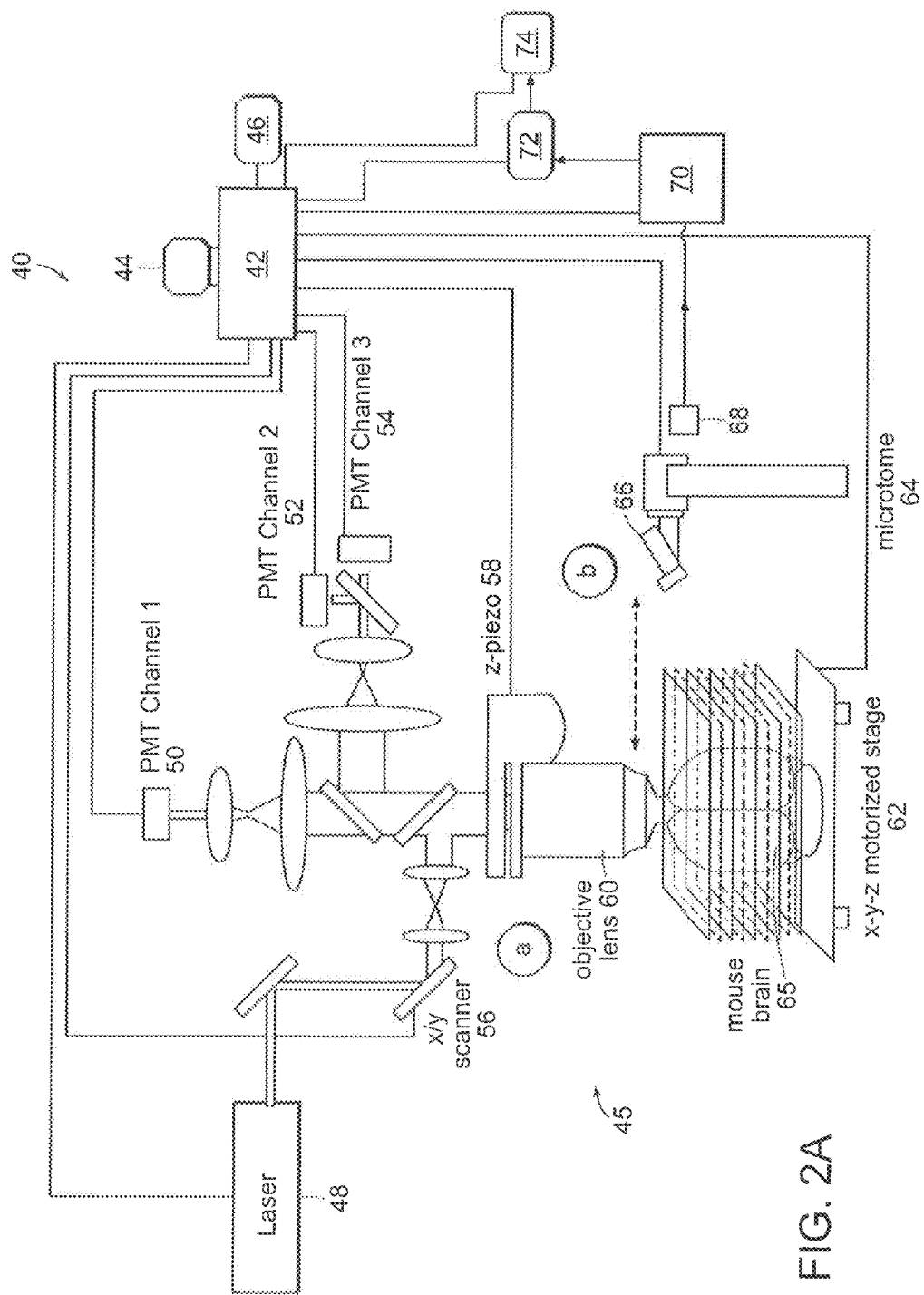
FIGS. 2A-2F illustrate a imaging and processing systems in accordance with preferred embodiments of the invention.

FIG. 2A shows an imaging and processing system 40 in accordance with the invention. A processor 42 is connected to system components including light source 48, a first PMT channel 50, second PMT channel 52, third PMT channel 54, (x,y) scanner 56, vertical scanner 58 that translates objective lens 60 relative to the tissue sample 65 (such as a whole organ mouse brain), sample motorized stage 62, microtome 64 with cutting tool 66, tissue section transport system 68 which moves each section of tissue to a storage system 70, a processing system 72 that further processes the section and a second imaging system 74 that can be used in combination with the first imaging system 45 to generate images of processed tissue. The images of the tissue, both before and after sectioning, can be stored in memory 46 and displayed in various formats as described herein on display 44. Additional details regarding imaging systems and methods of using these systems are described in U.S. Pat. Nos. 7,372, 985 and 7,724,937 and in U.S. application Ser. No. 11/442, 702 filed on May 25, 2006, the entire contents of these patents and application being incorporated herein by reference. Further details of systems and methods of detecting time resolved data used in conjunction with preferred embodiments of the invention are described in International Application No. PCT/US2009/060731, the entire contents of which is incorporated herein by reference. The processor 42 can be programmed with software that operates the system components and that processes image data as further described herein. The transport system 68 can move tissue samples for further processing and imaging as described herein. The processor 42 can then analyze image data from before and after sectioning to correlate and quantify data to characterize the tissue in detail. As sectioning can alter the surface morphology of the tissue, this can create difficulty in the process of correlating details in tissue structure after further processing and imaging. Preferred embodiments provide methods for analyzing image data from before and after sectioning in combination to characterize tissue.

Figure 2B:
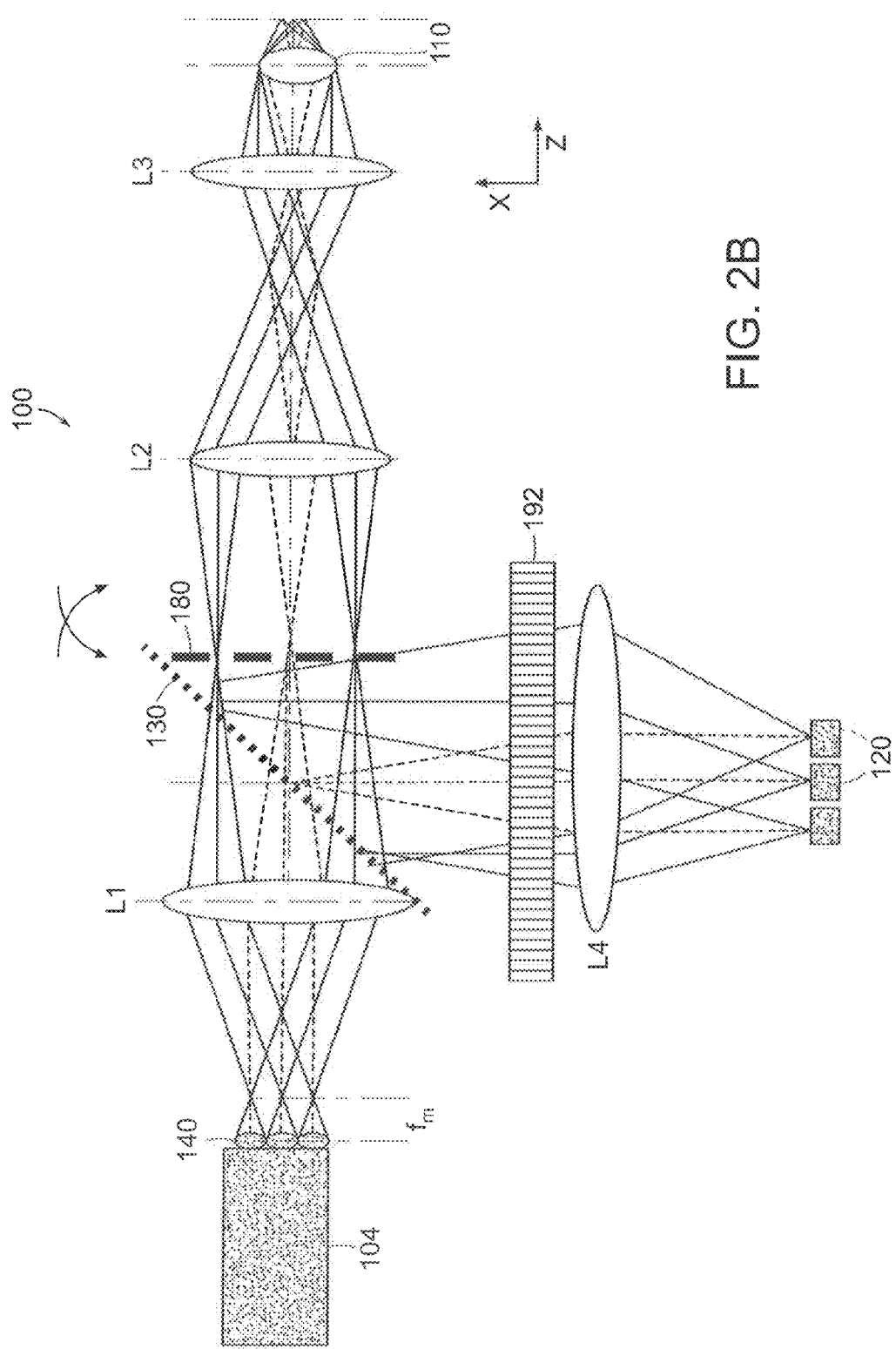
Figure 2D:
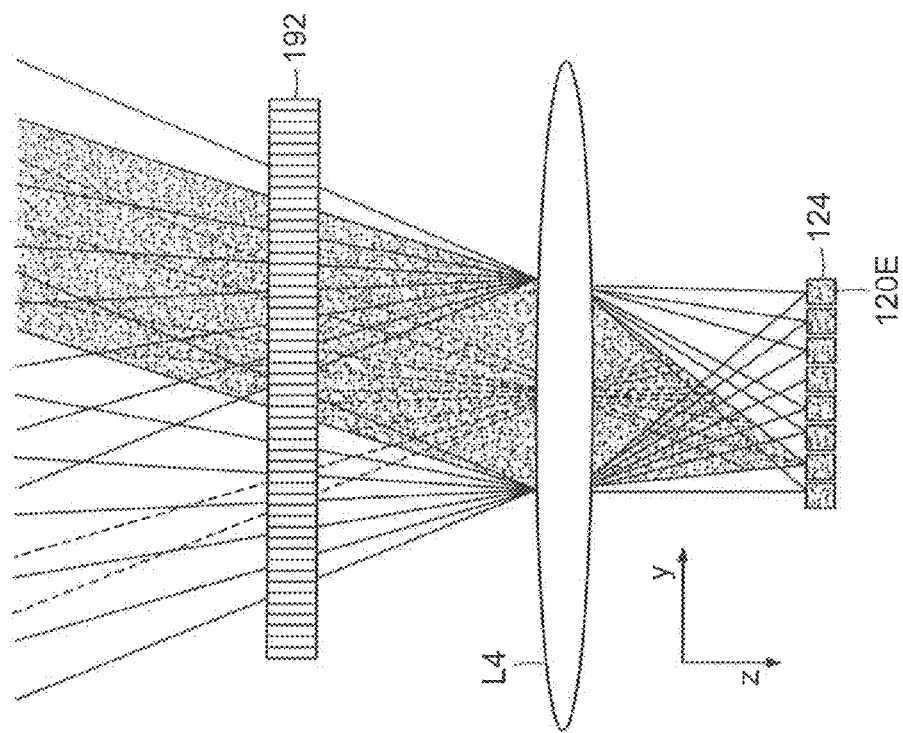
Figure 2C:
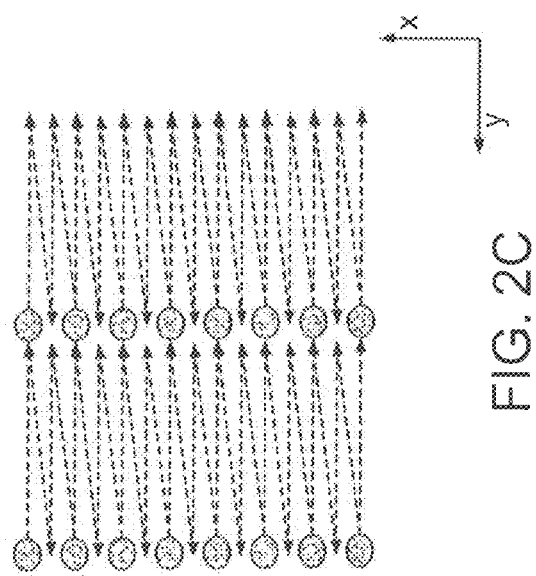
Figure 2F:
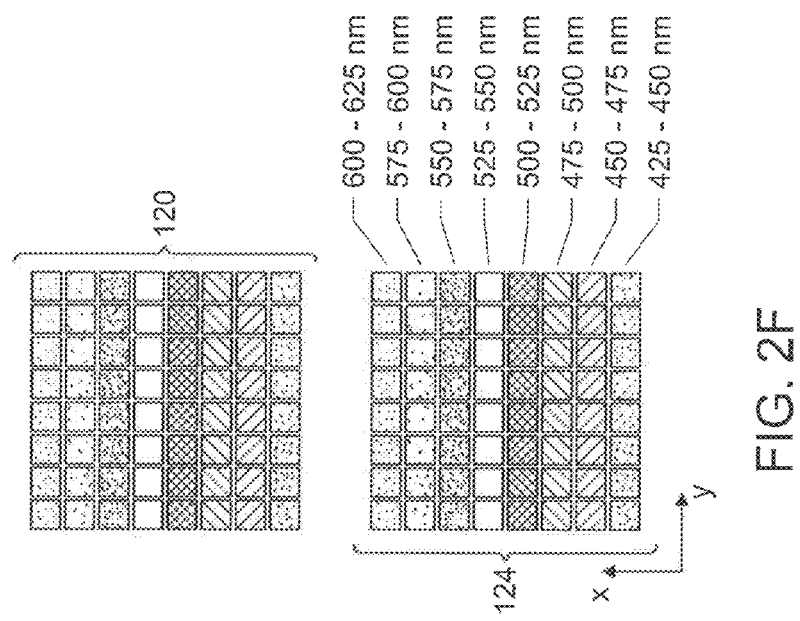
Figure 2E:
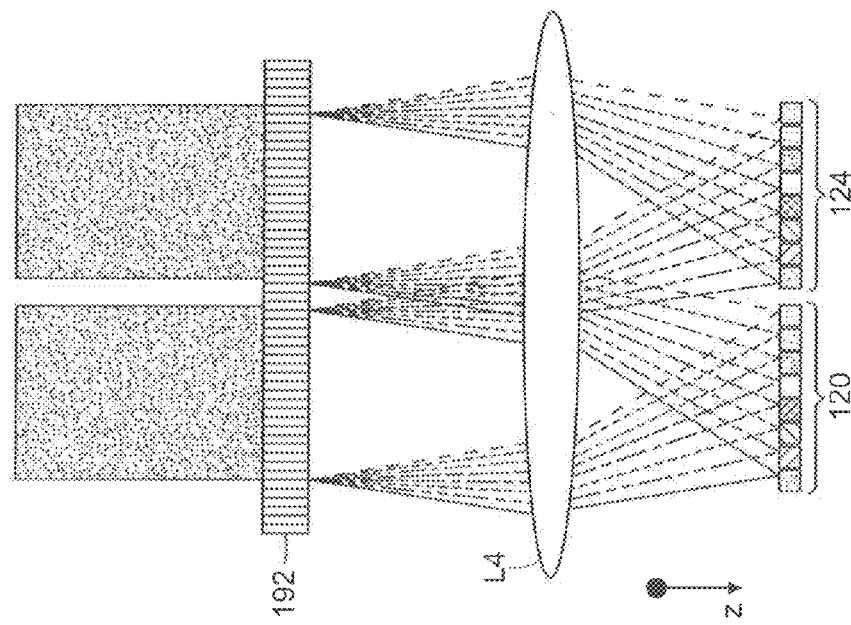
Figure 3:
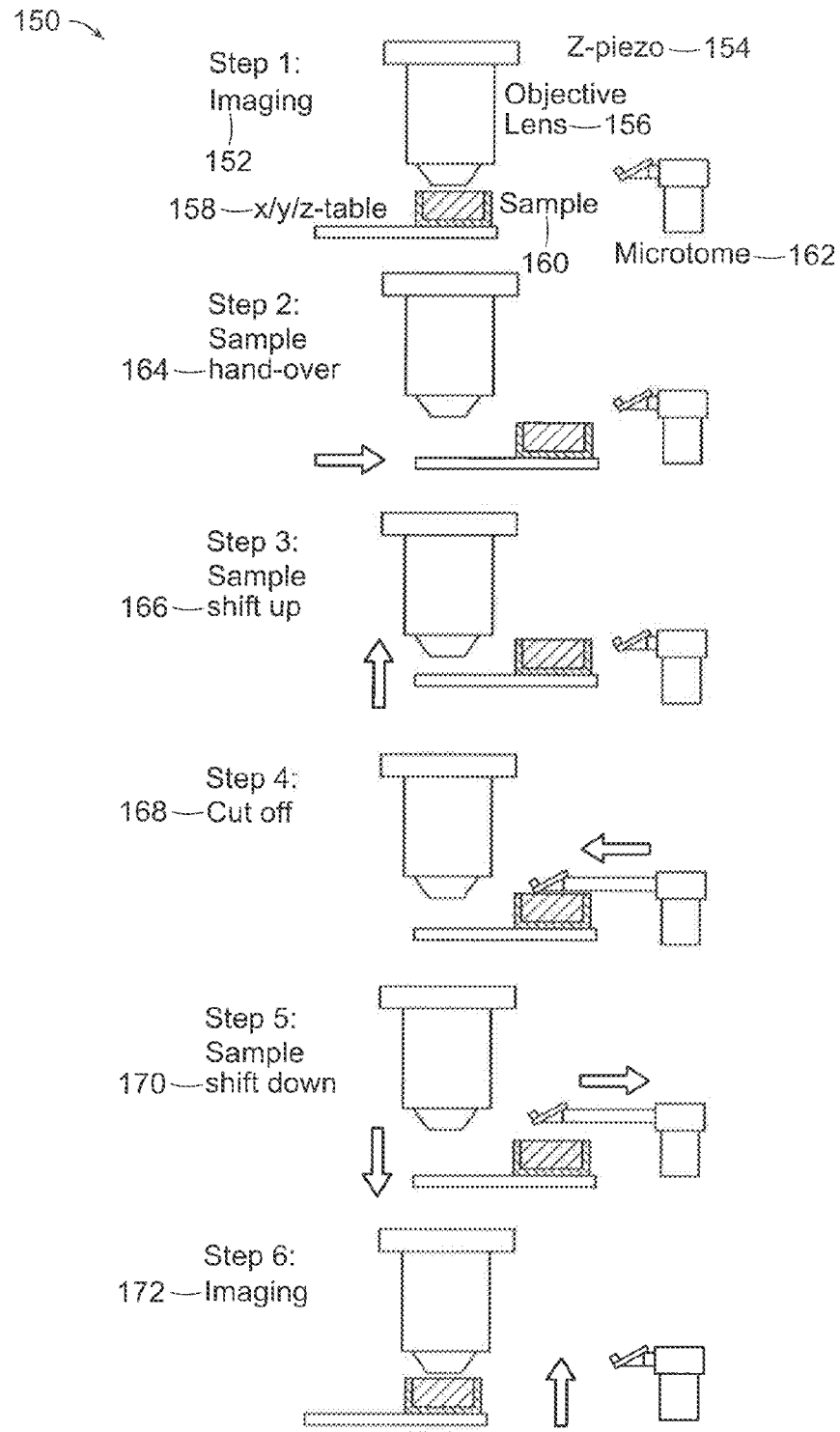
FIG. 3 illustrates a process sequence for imaging and sectioning of tissue in accordance with the invention.

A multiphoton imaging system 100 can be used in preferred systems and methods of the invention for imaging tissue before and after sectioning. Referring to FIG. 2B a further embodiment of the invention provides for multi color detection MMM 100 in the xz-plane. An array of 2×8 beams is generated by the micro lens array 140. The setup here is illustrated with two 1×8 beam lines. The distance between the foci in each line is determined by the combination of the source beam configuration and the micro lens array 140. Two light beams are conducted through the micro lens array 140 and intermediate optics L1 onto the focal plane of the microscope in which they create two lines of 1×8 foci. For simplified visualization, in FIG. 2D only 3 of the 16 beam traces in a 2×8 setup are illustrated. The full field is then scanned by the mirror oscillation of the scanning mirror 130, in which the scanning amplitudes need to be adapted to the distances of the foci. On the detection side a holographic diffraction grating 192 is incorporated that diffracts the multiple wavelengths emitted from the sample onto the photo-multiplier arrays of two stacked multi-anode PMTs 120, 124 (FIGS. 2E, 2F). In the setup the two multi-anode PMTs are stacked on top of each other, each serving as a spectral detection device for one line of 1×8 foci. The grating 192 properties (pitch/inch) and the focal length of the focusing lens (L4), which determines the distance between the grating and the multi-anode PMT, have to be chosen in accordance to the anticipated fluorescent probes used for staining the tissue sample. For this embodiment, a transmission grating 192 is used. Nevertheless, comparable and/or better efficiency can be achieved in embodiments that use a reflection grating or a prism. FIG. 2C illustrates the illumination foci and their scanning in the focal xy-plane.

Scanning is indicated for two arrays of 8 foci each. FIG. 2D shows the detection path of two beams projected in the yz-plane through grating 192 and lens L4 onto the stack of two AM-PMTs 120, 124. FIG. 2E shows the detection path projected in the xz-plane, where the beams are depicted passing through grating 192 and lens L4 with each of eight color bands being collected by the two AM-PMTs 120 and 124. FIG. 2F illustrates the anodes of the multi-anode PMTs 120, 124 in the x/y plane, showing that the 8×8 anode arrays of the detectors each detects one of the two 1×8 beam lines, where each 1×8 beam line has been diffracted by the grating 192E into eight color bands.

In order to cut the tissue, the system integrates a vibrating blade microtome into the high speed whole mount tissue scanner to allow automated retrieval of tissue sections for later processing such as immunohistochemistry (IHC) staining of the sectioned tissue slices. Vibrating blade microtomes, a variation of the basic microtome, are widely recognized as superior for cutting thick sections from soft or fresh tissue samples.

A vibrating blade microtome as the cutting device has several attractions. First it can section very soft materials such as unfixed brain tissue. Further, and in particular importance with regards to this invention, a vibrating blade microtome allows the preservation of tissue sections for later analysis, including IHC/FISH staining, mass spectrometry, microarray analysis, re-staining of the tissue with other dyes, and imaging with other modalities.

Further advantages of a vibrating blade microtome with regards to embedding in paraffin or other resins: 1. A vibrating microtome allows the tissue sample to embedded in an agarose gel, which has better preservation of GFP fluorescence as opposed to paraffin embedding: 2. Reduced tissue autofluorescence in comparison to paraffin embedded tissues: 3. Paraffin embedding has been shown to be of lower quality in tissue samples greater than 4-5 mm in extent, which can affect tissue morphology: 4. It is difficult to obtain quality sections with vascular casts that have been embedded in paraffin using a traditional microtome or milling machine.

Preferred embodiments use a standard cryostat or microtome to section frozen or paraffin embedded tissue, respectively, as the sectioning device. For instance, in cryosectioning, the key instrument is the cryostat, which is essentially a microtome inside a freezer. The microtome is capable of slicing sections as thin as 1 µm. The usual histology slice is cut at 5 to 10 µm. The tissue specimen is placed on a metal chuck and frozen rapidly to about −20 to −30° C. The specimen is embedded in a gel like media known as optimal cutting temperature compound (OCT). At this temperature, most tissues become rock-hard. Usually a lower temperature is required for fat or lipid rich tissue, and an even lower temperature for skin. Each tissue has a preferred temperature for processing but generally a temperature below 0° C. is required. Subsequently it is cut frozen with the microtome portion of the cryostat, the section is picked up on a glass slide and stained (usually with hematoxylin and eosin, the H&E stain). The preparation of the sample is much more rapid than with traditional histology techniques (around 10 minutes vs. 16 hours). However, the technical quality of the sections is much lower.

Further advantages of a vibrating blade microtome with regards to paraffin embedding: 1. It is difficult to obtain quality sections with PU4ii vascular casts that have been embedded in paraffin using a traditional microtome or milling machine: 2. Better preservation of GFP fluorescence for future studies employing transgenic animals: 3. Paraffin embedding of tissue has been shown to compromise GFP fluorescence: 4. Reduced tissue autofluorescence in comparison to paraffin embedded tissues: 5. Paraffin embedding has been shown to be of lower quality in tissue samples greater than 4-5 mm in extent, which can affect tissue morphology.

In one embodiment of the vibrating blade microtome 200 (often referred to as a vibratome) a flexure stage 206 can be employed (FIGS. 4A-4B). Flexure stages are high performance mechanical bearings which allow motion by the bending of a load element. Since they are constructed from a monolithic piece of metal, they have no internal moving parts and thus have excellent wear characteristics, and precise and repeatable ranges of motion. In general, motion control requires two separate functional units: a force generating unit, such as motor 204, to actuate the motion and a bearing unit, such as flexure arm 210 on which a blade holder assembly 208 is mounted, the arm 210 being attached to platform 212. This operates to constrain the motion to the desired trajectory. Flexure bearings use elastic deformation of materials to generate degrees of freedom to allow certain motions while minimizing all others. The allowed motions are determined by the geometry cut into the material of the bearing. Furthermore, it is possible to highly constrain the range of motion along a chosen axis. In the application at hand, motion in the z direction (into or out of the tissue sample) can result in poor quality sectioning. The vibrating blade 202 will have a peak to peak amplitude on the order of 2 mm. It is desirable to have a surface flatness of 1 micron which corresponds to stringent 0.05% requirement in the parasitic motion perpendicular to the cut plane. A flexure stage minimizes any such motions.

Figure 5B:
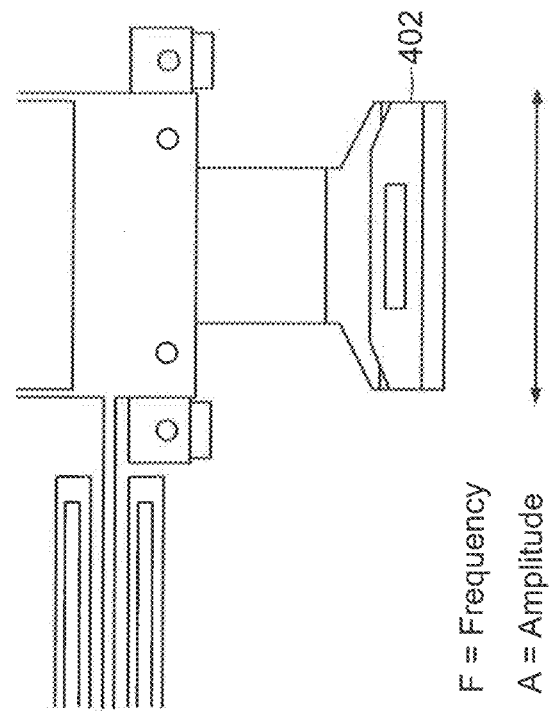
FIGS. 5A-5B illustrate tissue sectioning parameters in accordance with preferred embodiments of the invention.
Figure 5A:
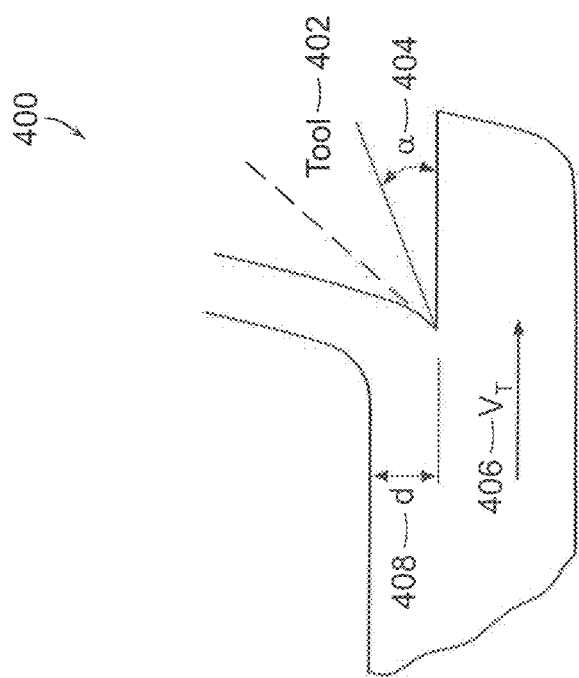

Vibrating blade microtomes introduce smaller cutting forces on the tissue because the back and forth motion of the blade presents an effectively sharper cutting profile, while still maintaining the structural strength and integrity of the blade in comparison to a blade with an actual narrower profile. The five important parameters 400 for cutting tissue are shown in FIGS. 5A and 5B. $V_T$ is the feed rate 406 of the material through the blade, d is the thickness 408 of the section, a is the tool cutting angle 404; F is the vibration frequency of the blade motion, and A is the amplitude of the blade motion. The amount of material removed per section is the following product:

$$M_{Removed} = d * Area * V_T$$

where Area is the cross sectional area of the tissue. The frequency and amplitude of the blade must be adjusted depending on the thickness of the tissue section, the feed rate, and the tool angle, and of the material properties of the tissue itself. In practice, good quality sections over a wide range (30-150 μm) of section thickness can be achieved by adjusting the cutting angle, feed rate and vibration frequency.

The blade holder assembly shown in FIGS. 4A and 4B is connected to the mounting platform through a flexure arm which allows motion along the direction indicated by the red dotted arrow. The blade holder assembly motion is actuated via a flexure linkage connected to the DC motor. The flexure linkage transforms the rotary motion of the DC motor (MCDC3006S, MicroMo, Inc.) to a harmonic linear motion with a frequency equal to the frequency of the motor. The flexure linkage is designed to minimize any forces transmitted to the blade holder assembly which are not co-linear with the desired linear motion of the blade. The frequency of the cutting motion can be set by adjusting the speed of the motor. The amplitude of the motion can be specified by adjusting the connection of the flexure linkage to the DC motor through a slotted linkage on the motor. The razor blade (stock 2.5"×0.3" carbon steel) is fastened to the blade holder assembly through a micro flexure which securely clamps the razor blade. The blade angle α can be adjusted by rotating the blade holder and locking it to the blade holder assembly.

The microtome specifications are characteristic of the mechanical response of the system and can be verified using a 2-axis laser range finder to monitor the motion of the blade and XYZ axis stage. The MCDC3006S motor speed performance is operating using an integrated rotary encoder. The defect rate can be established by sequential cutting of 254 sections of 100 micron thickness (1" total depth). Five separate runs can be performed for a total of 1270 sections. The section surface quality of a 5 mm×5 mm area can be verified by post-sectioning with 3D two photon imaging of the surface of the heart tissue which will be en face stained with fluorescein. The resulting 2D surface image can fit and the RMS deviation of the average surface position calculated.

TABLE

Milestones

Tissue: Rabbit myocardial

| Microtome Specifications | |
|---|---|
| Feed rate | 0.1-10 mm/s |
| Vibration Frequency | 25-200 Hz |
| Vibration Amplitude | 0.1-2 mm |
| Section Thickness | 10-100 μm |
| Blade angle | 5-20 degrees |
| Parasitic z-motion | 1 μm |
| Cutting Characteristics | |
| Surface Quality | 2 μm RMS |
| Defect Rate | <1 defect in 1270 |

The system and methods in U.S. Pat. No. 7,372,985 describes a technique for obtaining images of a thick tissue the entire contents of this patent being incorporated herein by reference. Briefly, U.S. Pat. No. 7,372,985 describes systems and methods that combine optical and mechanical sectioning to obtain images of whole mount thick tissues.

In this present invention, systems and methods are used to capture the tissue sections which are removed from the whole mount tissue, and to map additional biochemical and morphological information onto the whole mount tissue by analysis of the captured tissue sections.

While direct intravital tissue labeling, transgenic animals, native tissue autofluorescence, and SHG contrast provide powerful methods to visualize the complex 3D biochemical environment within a tissue, there are still a large number of biochemical states and signatures which are only possible to examine by other methods, such as immunohistochemistry (IHC) staining. Unfortunately it is very difficult or impossible to reliably IHC stain whole mount tissues greater than approximately 100 microns in depth. This is due to the large size of antibodies used in IHC staining and their subsequent slow diffusion and steric hindrance within the tissue. Therefore there exists a great benefit to save the sections after they have been removed from the whole mount tissue for further biochemical analysis. Further examples of analysis are, without limitation, FISH, mass spectrometry, imaging mass spectrometry, PCR, micro dissection.

In addition, once the tissue has been sectioned, the tissue slice can often be much more easily stained with additional dyes. For instance, even whole mount staining of, for instance, a mouse brain or heart, with a dye is generally not possible. In these cases, the exterior portion of the organ is often much more strongly stained while the inner portions weakly or not stained at all due to the problem of diffusion of the dye through a thick tissue. This is even true for small molecule stains such as DAPI or Hoescht 33442. Other important dyes include dyes used in standard H&E. By staining or re-staining the tissue after it has been sliced, it is possible to use both a far wider range of dyes and more homogeneous staining, and generate more types of contrast to identify various tissue constituents.

In addition, due to limitations or configuration of the imaging device used in the whole mount imaging procedure, it may be desirable to image the captured tissue slices on a separate type of imaging instrument. For instance, some dyes or intrinsic molecules are better imaged using one-photon confocal microscopy rather than multiphoton, or vice versa. Other modality examples include OCT, CARS, SHG, STED wide field and time resolved fluorescence.

One strategy is diagnostic comprehensive imaging of whole mount tissues, followed by comprehensive processing, imaging, and indexing every captured tissue section. Alternatively, the imaging process can be followed by selective IHC/FISH staining of individual sections of interest. Another method is selective imaging of a region of interest (ROI) of a whole mount tissue followed by processing, imaging, and indexing of captured tissue sections.

Figure 6:
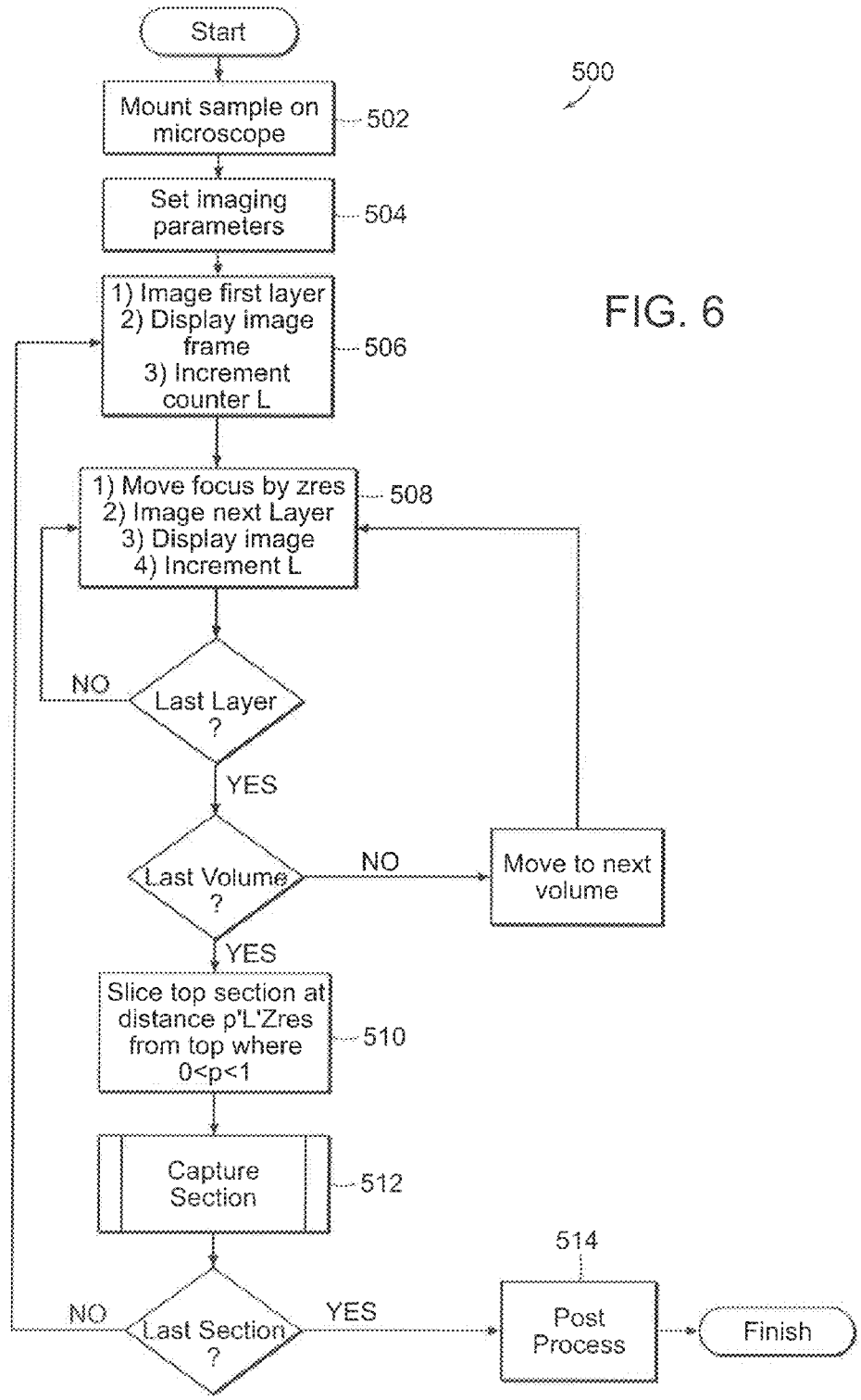
FIG. 6 illustrates a process sequence of methods used in imaging tissue.

FIG. 6 is a flowchart describing the steps 550 involved in capturing a tissue section from a whole mount tissue. The sample is mounted 502, imaging parameters are selected 504. After the uppermost portion of a tissue block has been imaged 506, 508, the uppermost portion is removed 510 from the tissue with a sectioning device, such as a vibratome. This section is captured 512 by a tissue retrieval device and transferred to a suitable chamber for storage. The imaging and sectioning procedure continues such that at the end, not only are images of the tissue obtained, but also the sectioned tissues have been saved, indexed to their original position in the tissue, and transferred to a collection chamber for each tissue block. The system then performs further processing 514 as described herein.

Figure 7:
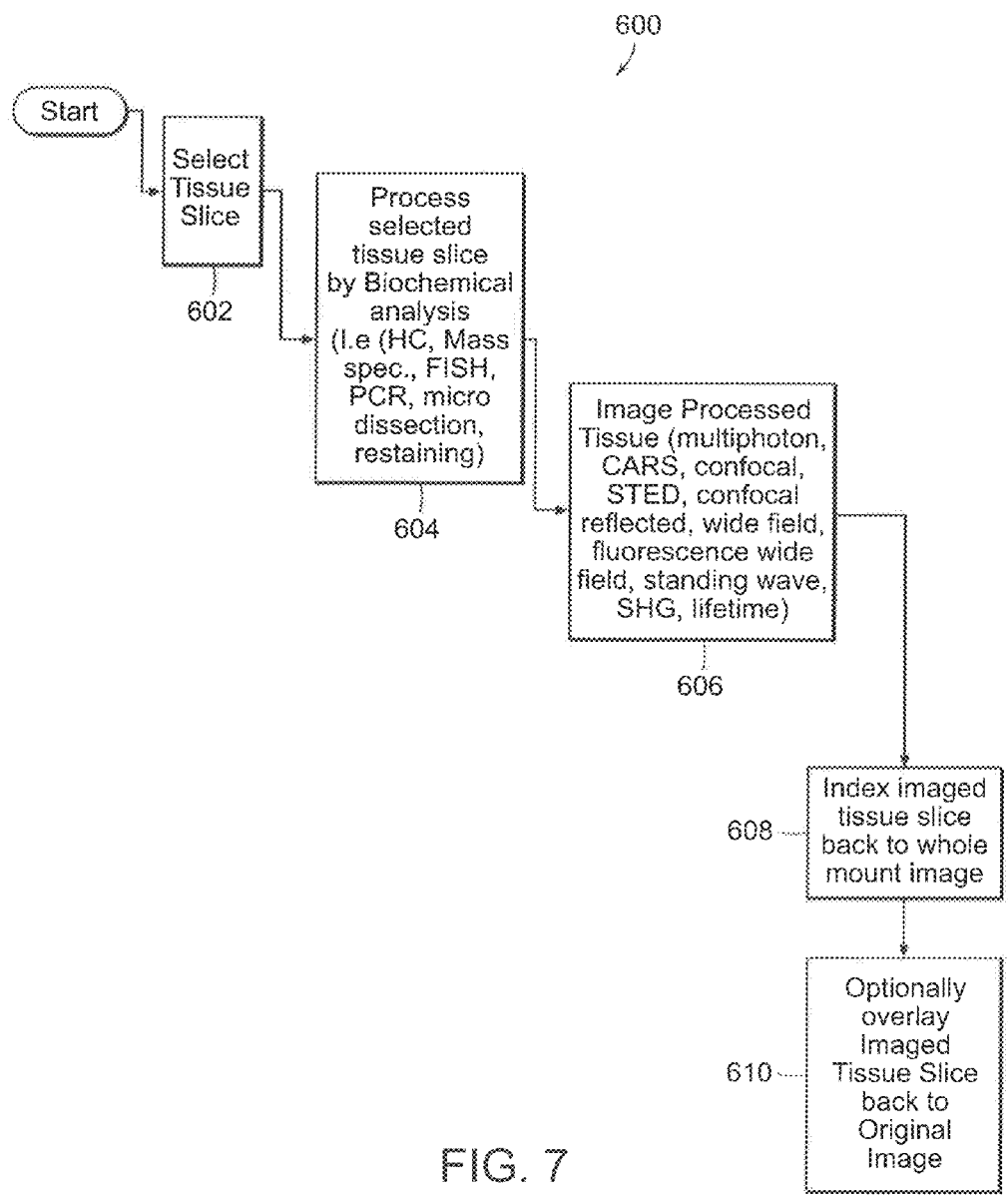
FIG. 7 illustrates a process sequence processing of a plurality of images of a tissue sample.

FIG. 7 is a flowchart describing the process of processing the captured tissue sections, re-imaging the tissue sections by a method or variety of imaging methods, and then indexing these obtained images back to the original images obtained from the imaging of the whole mount tissue. In this way, it becomes possible to recover additional information about the biochemical state or morphology of the original tissue block which was not possible previously. Each section is selected 602, processed 604, imaged 606, indexed 608 and analyzed in combination 610, such as by overlaying.

In comparison to current state of the art practices, tissue sections may be retrieved from a standard vibratome, but there exists no easy method to relate the tissue sections back to the original, un-sectioned tissue block. Serial section analysis, for instance, is currently in use by many laboratories, but it has proven very difficult to generate, say, 3D datasets of IHC stained tissues due to the difficulty of processing and imaging post sectioned tissues. Problems include mechanical distortion of the tissue, and difficulty in aligning successive sections of a tissue. The described invention allows, for instance, IHC stained tissues to be morphed back to an original pristine tissue block which serves as a reference. The process of registration can include rigid rotation and translation of each pixel in an image, morphing and/or non-rigid transformation. A preferred method can include a scale invariant feature transform (SIFT) registration process. In this process, a plurality of features contained in the overlap region (FIG. 1H) are used to define a transformation to map pixels in a post-sectioning image to achieve stacking and alignment.

Figure 8:
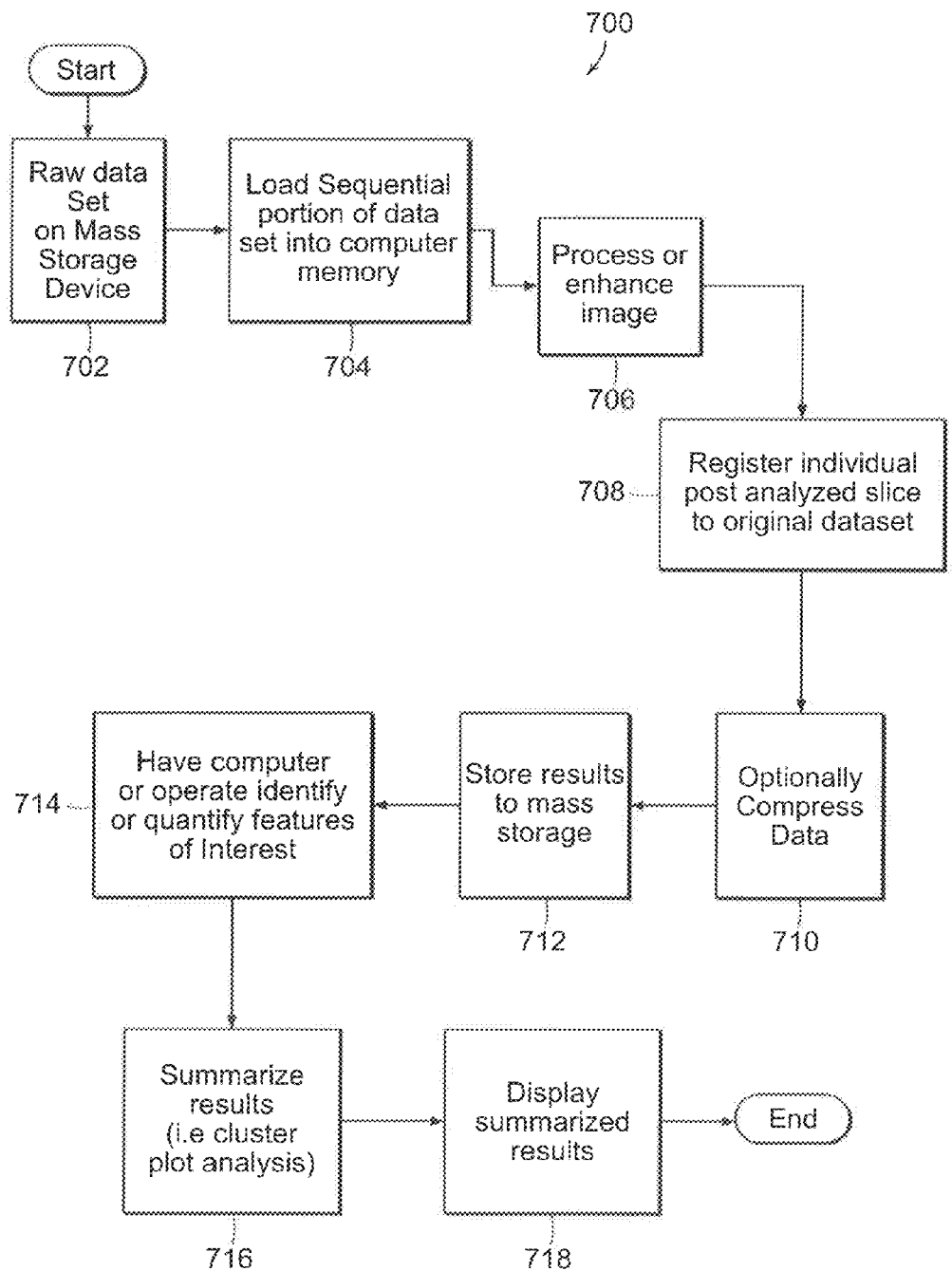
FIG. 8 illustrates a process sequence for analyzing image data.

FIG. 8 is flowchart describing steps in the process 700 of taking the imaged tissue slices and registering them back to the original whole mount dataset. The image data is retrieved from memory 702, loaded sequentially into computer memory 704, processed an/or enhanced 706, registered to original unsectioned image data 708, optionally compressed 710, stored 712, identify and/or quantify features of interest 714, summarize results (graphically) 716 and display 718 the data and results on display 44 or transmit to remote locations via a network.

Figure 9:
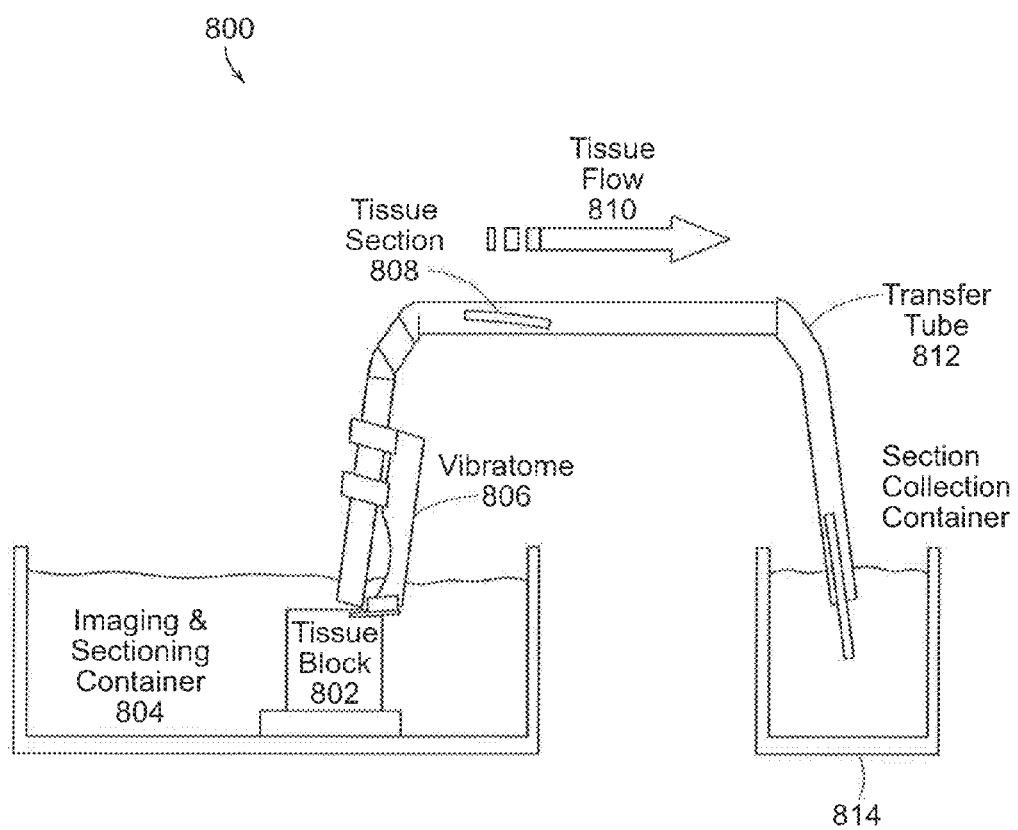
FIG. 9 illustrates a system for distributing sectioned samples for further processing.

A preferred embodiment uses a tissue recovery unit 800 shows in FIG. 9 for tissue slices 808 which have been removed from the tissue 802 by the microtome system 806. A tube 812 can be used with a fluid flow 810 or mounted on a tape to move the sections from imaging container 804 to collection container 814.

A major technical risk is the initial collection of the tissue slice and transfer to a collection chamber. The unit captures and transfers individual slices. In other embodiments, a rotating collection chamber can be incorporated which enables every slice to be saved in its own indexed container.

During the tissue recovery process the tissue is sectioned from the whole mount tissue block at a pre-specified thickness. During the sectioning process, the tissue sample is moved by the sample stage on which the bath is mounted toward the blade and the vibratome blade vibrates perpendicular to the line of motion. The transfer tube is mounted near the vibratome which ensures its fixed position in regards to the tissue surface and blade during the cutting process. A flow of liquid, such as saline solution, is flowed thru the tube to induce the sectioned tissue to travel along the transfer tube to a collection chamber. After the sectioning is complete, the section is transferred along the tube. and to the collection container. The flow liquid through the transfer tube is generated by a pump as shown in FIG. 9.

Figure 10:
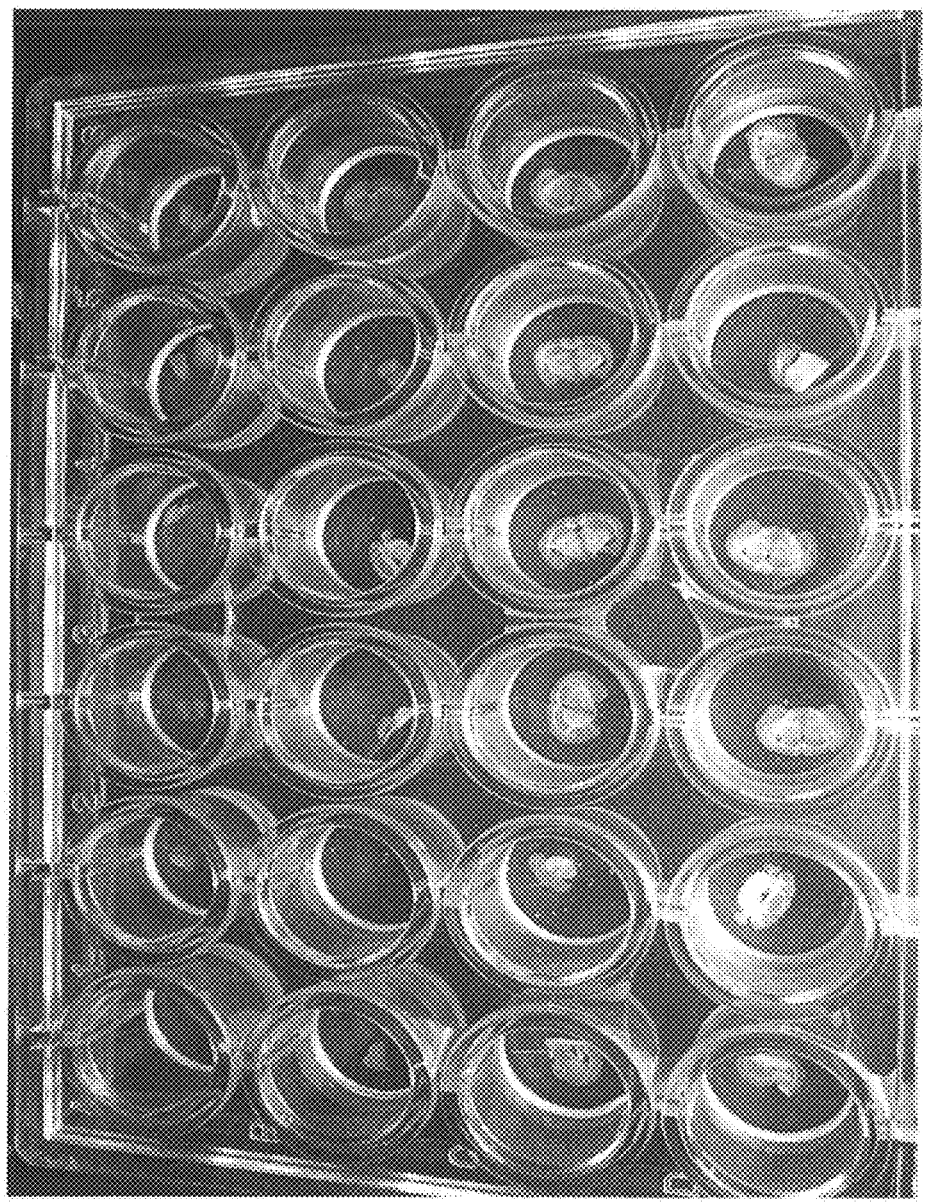
FIG. 10 illustrates a system for separating tissue sections for further processing.

An example of capture slices from a tissue block are show in FIG. 10 where coronal sections from a mouse brain have been transferred to a well plate array 820 with one section per well. The sections are ready to be further analyzed by a variety of techniques including IHC.

Angiogenesis is the sprouting of new blood vessels from existing vasculature. It is a major component of the two biggest killers in the United States today, heart disease and cancer. Despite the importance of angiogenesis to biomedicine, angiogenesis therapies have been difficult to develop due to the lack of effective assays. Individual angiogenesis assays on the market focus on narrow aspects of angiogenesis and are too often performed under in vitro conditions or in other model systems with low physiological relevance. They fail to capture the complex, multistep 3D nature of angiogenesis which is strongly dependent on interacting components specific to the microscopic tissue under study. Additionally current assays suffer from low throughput and are unsuitable for integration into drug development programs.

This invention describes a novel angiogenesis assay, which is based on a device with includes a vibratome, a tissue section capture device, and tissue labeling and analysis. Furthermore, the captured section can be reimaged and overlaid onto the original 3D tissue structure under inspection. This enables analysis of IHC stained thick tissue having a depth of several millimeters. Its advantages include high speed, automation, and physiological relevance. The invention can incorporate high speed multiphoton or confocal microscopy. It provides ex vivo imaging of macroscopic portions of tissue up to entire organs in small mammalian models. It has both subcellular detail and multispectral resolution. The system can be used for pharmaceutical development where it is necessary to screen tens to hundreds of late stage drug candidates for target validation and efficacy.

Cardiac ischemia the leading cause of death in the United States. While angiogenic therapies hold much promise for the treatment of ischemic heart disease, they have not delivered on this promise, mostly due to the complex nature of the angiogenic response, particularly at the microscopic level. We use this invention or assay by studying the angiogenic response of myocardial tissue to exogenously applied bFGF in infarct models. Additionally, the system correlates the in situ angiogenic response to the tissue collagen content, nuclei distribution, and hypoxia state.

Angiogenesis is the formation of new blood vessels from pre-existing vasculature. It is a central component of many diseases including myocardial ischemia, cancer, diabetic retinopathy, macular degeneration, and rheumatoid arthritis. Angiogenesis has been characterized as a potential 'organizing principle' in biology, where an understanding of angiogenesis mechanisms will have broad therapeutic applicability across a range of diseases. It has been emphasized that the enormous potential of angiogenesis based therapies stating, Angiogenesis research will probably change the face of medicine in the next decades, with more than 500 million people worldwide predicted to benefit from pro- or anti-angiogenesis treatments.

Unfortunately, the development of new angiogenesis therapies is plagued by the ambiguity, low throughput, inconsistency, and importantly, the low physiological relevance of current angiogenesis assays. As such, there exists an enormous biomedical need and market opportunity for better, quantitative assays which can provide insights that are readily transferable to the clinical setting or the next round of the drug development cycle. Innovative highly relevant, tissue based assays can replace many of the contemporary histopathological practices rooted in techniques decades old.

Ischemic heart disease is the leading cause of death in the United States. It is caused by reduced blood flow to myocardial tissue, leading to reduced heart function. Angiogenic treatment by recombinant protein growth factors to induce revascularization has long been recognized as an attractive alternative to traditional bypass surgery. Angiogenic agents such as the fibroblast growth factor (bFGF) or the vascular endothelial growth factor (VEGF) families induce a strong angiogenic response in myocardial tissue in animal models Based on these observations, high hopes were placed on subsequent human clinical trials. Unfortunately results from these trials have proved ambiguous and mostly disappointing. Intracoronary and intravenous VEGF infusions lead to no difference with placebo at 60 days and only ambiguous results at 120 days. Similarly, intracoronary bFGF did not improve exercise tolerance or symptoms compared to placebo. Continuous delivery strategies have only been slightly more encouraging. Intramyocardial injections of bFGF alone or in heparin-alginate microspheres in patients undergoing bypass grafting appeared to improve symptoms and capillary density, but these trials were small and confounders, such as the impact of the revascularization procedure itself, complicated results. It is becoming evident that effective angiogenesis requires sustained presence of an appropriate growth factor mixture in the local milieu or nascent capillaries will tend to otherwise regress. Nevertheless, it is unclear whether myocardial growth factor concentrations adequate for angiogenesis have in fact been sustained in each of the clinical trials.

Indeed, knowledge of the local pharmacokinetic processes governing uptake and distribution of growth factors in a highly vascularized tissue such as myocardium is limited. The effects of mass transfer into and convection within capillaries may so locally influence growth factor concentrations that the rate of angiogenesis might bear no relation to mean myocardial drug concentrations.

Myocardial tissue itself changes in response to angiogenesis, and the consequences of the continuous formation of blood vessels on the ability of locally delivered drug to sustain nascent vessels have not been examined. As such, even the basic question of whether growth factors are best administered in ischemic vs. healthy vs. borderline regions—or whether site of administration is irrelevant—remains unanswered. With the surge in interest in therapeutic angiogenesis, characterizing the vascularization response across the myocardial wall becomes of pressing importance.

The growth of the microvasculature in angiogenesis occurs in a complex series of tightly coordinated events: 1) activation of endothelial cells within the existing vascular 2) disbanding of the capillary basal lamina lining the vascular wall 3) capillary sprout formation and endothelial cell migration 4) extension of sprouts and vessel tubular formation by endothelial cell proliferation 5) vessel maturation including basement membrane formation and recruitment of pericytes along the newly formed vascular and 6) initiation of blood flow and remodeling of the neovascular network. It is very difficult to study all these steps in a single assay, and thus many different in vitro and in vivo angiogenesis assays have been developed, each hoping to capture an aspect of the angiogenic cascade.

Current angiogenesis assays on the market by examining the most popular in vitro and in vivo assays, and then review the current state of the art of histological analysis of angiogenesis.

In Vitro Assays:

Endothelial cells play a central role in angiogenesis and many in vitro assays are based on endothelial proliferation, migration or tubular formation in response to an angiogenic factor. The advantages of these assays are their low cost, simple use, high reproducibility and easy quantification. They have proven valuable as early screening tools for angiogenic activity. However, endothelial 2D cell culture assays have significant drawbacks: First, endothelial cells are highly heterogeneous. Phenotypic differences have been noted between endothelial cells taken from capillaries and those taken from large vessels. Inter-organ differences exist as well with endothelial cells that are part of the blood brain barrier as one example. Furthermore, flow and matrix conditions in culture can significantly affect results as well, and differences in endothelial cell karyotype and activation state in culture have also been observed. Most importantly however, fundamentally in vitro assays are gross simplifications that fail to capture the interacting nature of the endothelial cells with the surrounding tissue stroma and thus must always be used in conjunction with in vivo assays if to be useful.

In Vivo Assays:

In vivo assays attempt to capture the complex spatial and biochemical character of the angiogenic response. The three most popular include the CAM, matrigel, and the corneal eye pocket assays. In the CAM assay, angiogenesis is monitored on the chick embryo CAM membrane. The assay is simple and inexpensive to conduct, and lends itself to large scale screening. However it is sensitive to environmental conditions, particularly $O_2$ concentration, and it can be difficult to quantify vascular growth due to the difficulty in visualizing new vessels reliably. Additionally, inflammatory responses can confound results. 2) In the matrigel assay, liquid angiogenic agents such as a drug or tumor cells are injected into a liquid matrigel which is then subcutaneously injected into an animal where it solidifies. Host cells and vascular permeate into the gel and tare later removed and quantified by measuring hemoglobin content or by histological examination. The assay is technically easy and quantitative. However disadvantages beyond expense the ill-defined biochemical matrigel composition, inflammation and chamber geometry all make interpretation difficult and limit the usefulness of the assay 3) The cornea assay is based on the placement of an angiogenic inducer into a corneal pocket in order to evoke vascular outgrowth from the peripherally located limbal vasculature. In comparison to other in vivo assays, this assay has the advantage of measuring only new blood vessels, because the cornea is initially avascular, and the non-invasive monitoring of the angiogenic response. Significant drawbacks include inflammation at the injection site, the technical difficult nature of the surgery, and the atypical nature of the normally avascular cornea, all which affects the relevance of the assay.

Histological Examination:

Given the limitations in vitro and in vivo assays, many researchers have opted for direct histological evaluation of angiogenesis. Tissues are 2D sectioned and then IHC stained for endothelial cells along vessel which serve as a marker for vasculature. In principle this can provide a direct route for quantifying the vasculature; however in practice it suffers from significant limitations: 1. The IHC staining for the endothelial cells is not always effective or homogeneous, leading to significant ambiguity 2. Patent vessels cannot be discriminated from non patent vessels 2. Only 2D information is provided and vessels which cross the examination plane multiple times cannot be taken into account 3. Information about the 3D vascular network architecture is completely lost 4. The manual image inspection process is laborious 5. By the necessity of the labor intensive nature, sparse sampling must be employed. 6. Many months of training are required 7. Quantitative comparison between different observers is difficult.

In summary, while the specific limitations of the current assays are myriad, the underlying cause of these weaknesses is the complex nature of angiogenesis: a multistep 3D process occurring in situ on the microscopic scale, with a spatially varying biochemical microenvironment, and strong dependence on the interacting components specific to the tissue under study. Further complicating matters, most assays are based on simple measures of changes in vascular density or extent, despite therapeutic efficacy depending on microvascular patency and interaction with the surrounding 3D tissue stroma as well. As a result, current angiogenesis assays have serious shortcomings and are either poor predictors of how well an angiogenic therapy will perform in the clinical setting, or are too costly and lack necessary throughput.

Pharmaceutical companies are currently investing vast resources in developing new angiogenic drugs and therapies. It is currently estimated that the cost of developing a new drug is $802 million and takes approximately 12 years (21). Given that the life of a patent is only 20 years, pharmaceutical companies often have as a little as six to eight years to recoup not only the costs of developing the drug but of all drug candidates which did not make it through clinical trials. It has been estimated that it costs a pharmaceutical company approximately $1 million per day for every day that a successful drug is delayed to market. There is intense pressure to find new ways to reduce the costs and times to develop new drugs. In 2006 over 43 different drugs with anti-angiogenic effect were estimated to be in various stages of development. Pro-angiogenic therapies are also actively being developed for treating hypoxic tissues resulting from occluding lesions in coronary or cerebral arteries in the heart and brain respectively.

The assay described herein can be used in the late drug development cycle with animal model testing. It has the potential to provide crucial, contextual information at the physiologically relevant level to see which drugs work, and just as importantly which drugs should be abandoned before the start of expensive clinical trials. Key stumbling blocks which have been holding back more tissue based studies are the lack of automation, high throughput and ease of use and most importantly, relevance.

Robust vascular segmentation requires large S/N (signal to noise ratio) levels. In high speed imaging, this can be challenging to achieve due to low pixel residence times. Vasculature casting is an attractive alternative labeling protocols which label the vasculature wall. It provides far higher signal levels.

Additionally vibrating blade microtomes can section vascular casts. Vascular casting is an attractive method to image the morphology of a vascular tree since polymer vascular casts have very high signal levels in comparison to vascular wall labeling strategies. These high signal levels allow fast imaging with pixel residence times on the order of 0.5 µs, but still obtain sufficiently high vascular signal levels for automatic segmentation of the vascular network.

In vascular casting, a polymer is injected into the animal and fills the entire vascular tree and polymerizes into a solid. Since the entire volume of the vessel is labeled and not just the vessel wall signal levels can be very high and thus suitable for automated segmentation.

Mercox and Batson's no. 17 are two of the most popular casting agents but lack inherent fluorescent contrast. Additive fluorescent dyes exist for the agents, but degrade in cast performance, preventing it from penetrating into the smallest vessels. Additionally, they become very brittle after curing. Initial tests have shown that mechanical stress imposed by whole mount milling or sectioning of tissues causes fractures deep within the tissue. The resulting discontinuities in the vasculature tree make them an unfavorable choice for a casting agent. However, a new casting material, PU4ii (vasQtec, Zurich) has been recently developed. It is well suited for fluorescence microscopy and has been shown to be effective in labeling the smallest capillaries. Beyond its material properties, its main attraction for this application is that it can be mixed with fluorescent dyes and made extremely fluorescent. Thus, preferred embodiments utilize a fluorescent casting material.

The resin has been used with a multi-photon imaging system by performing whole body perfusion castings of both mice and rabbits. The casting is followed by a perfusion and fixation protocol. For the mouse casting, access is gained through the apex of the left ventricle of the heart with a 21-gauge cannula and secured in place with super glue. The right atrium is punctured to allow outflow of the perfusate. All perfusion solutions are warmed to 37° C. in a water bath prior to use. Perfusion (~20 ml) physiological NaCl is performed until all blood is flushed from the animal. Following, the tissue is fixed by perfusion with 20 ml of 4% paraformaldehyde (PFA) in PBS, through the systemic circulation. Intravascular fixation is followed by the casting material.

Immediately after the perfusion and fixation the cast is mixed with hardener (0.8 ml) to the mixture of PU4ii resin (5 ml), solvent (2-Butanone (MEK)) (4 ml) and dye (7.5 g). The liquid is stirred briefly and then injected into the animal through the same cannula the perfusion and fixation was performed. To remove small air bubbles in the resin, the final mixture is set under vacuum for 2-3 minutes using a standard vacuum chamber. At the time of injection the casting material has a consistency of water.

Using the vibratome and tissue retrieval system images are taken through a 5 mm×5 mm×5 mm portion of tissue with 1 µm radial resolution and 2 µm axial resolution in under 2 hours and recover the skeletal geometry of the vasculature tree with an automated thresholding algorithm.

Previous studies of infarct models have shown that the pro-angiogenic factor bFGF administered via a sodium alginate polymeric patch induces a strong angiogenic response in treated rabbits versus untreated controls. A marked increase in vascular density near the region of the patch was observed by Day 2 and 8 (FIG. 12C). By Day 30 however, the vascular density (FIG. 12B) tended to regress to initial levels (FIG. 12C). These results were obtained by histological examination of the heart tissue after imaging and sectioning (FIG. 11). Due to the time consuming nature of the inspection procedure, four 10 µm thick sections were chosen at 2 mm intervals from the apical end (FIG. 12A). These sections were IHC stained for endothelial cells and the vasculature density established by manual counting.

There were several limitations of the analysis. Traditional histological examination of IHC stained tissues is time consuming and became the rate limiting step. IHC patterns were often difficult to interpret and consistent results between different examiners were hard to obtain, making comparison between different studies at different times problematic. Additionally, with IHC staining all endothelial cells are labeled, including both patent and non-patent vessels. Further, 2D sections sacrifice all information about the 3D vascular network. These factors lead to difficulties in using the recovered vasculature patterns for models of vascular flow and drug uptake, which in turn severely hindered the development of new delivery strategies.

Figure 13:
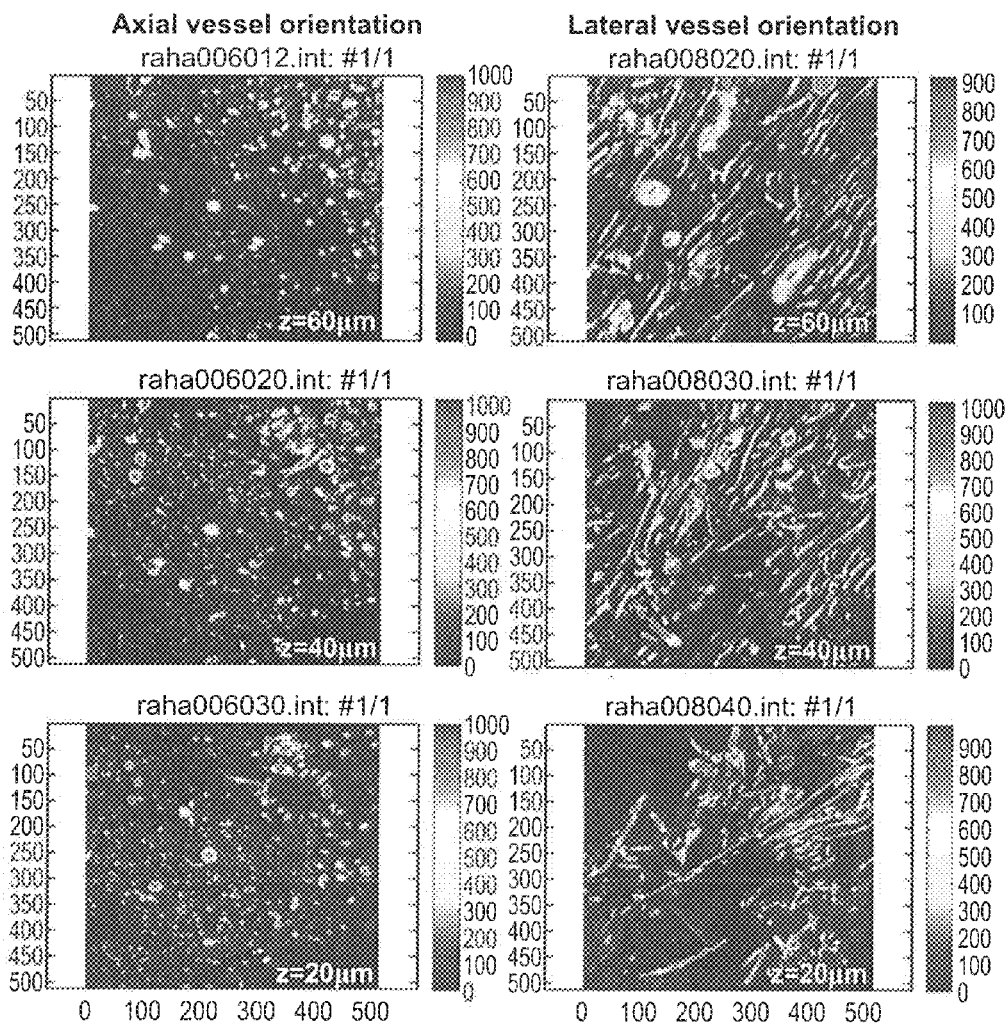
FIG. 13 are images of a vascular casting process.

This process can confirm the results for Day 2, 8, 30 shown in FIG. 13, where an initial increased vascular density was observed which subsequently decreased to initial levels by day 30.

Besides the vascular network, the system can image nuclei, tissue collagen content (through SHG imaging), and tissue autofluorescence. In addition the hypoxia marker EF5 can be imaged on every tenth section (1 mm) via IHC staining of the recovered slices. This provides a total of at least 5 spectroscopically distinct components.

In-Vivo Myocardial Drug Delivery New Zealand White rabbits (3-3.5 kg) can be anesthetized with an intramuscular injection of 35 mg/kg ketamine and 5 mg/kg of xylazine. Rabbits are intubated with a 3.0 mm endotracheal tube for inhalant anesthetics and positive pressure ventilation. The level of anesthesia is maintained with isofluorane between 1-3%. The skin over the chest is shaved and sterilely prepared with Betadine and alcohol. In preparation for a thoracotomy, a pre-emptive line block of Lidocaine will be administered along the surgical incision. A left thoracotomy will be performed to gain access to the heart. A clamp is used to keep the chest open throughout the procedure. A small opening in the pericardium can be created while care will be taken to minimize the damage to the pericardium. The left anterior descending coronary artery is located and ligated with a suture to create an ischemic heart model, with successful induction of ischemia documented by elevations of the ST segments on simultaneous continuous ECG recording. bFGF bound heparin sepharose beads can be placed in the pericardial space. The pericardium is kept closed with suture to prevent leakage of bFGF. The thoracotomy and skin incision is then be closed. A positive end expiratory pressure and negative pressure chest tube will be used during closure to prevent pneumothorax. An injection of 0.03 mg/kg buprenorphine will be given subcutaneously every 8 hours for first 72 hours for analgesia. Control animals receive heparin sepharose beads embedded sodium alginate polymeric devices without growth factor.

The hearts are then dissected from the animal and perfusion casted with PU4ii through the main artery as is described herein. In addition the nuclei are perfusion labeled with 20 ml Hoechst 33342 (100 micro g/ml). The Hoechst labeling step is included in the perfusion procedure after the heart was flushed with PBS but before it is fixed and casted. It is not necessary to label collagen as that will be detected by intrinsic second harmonic generation (SHG). In order to directly assess tissue hypoxia states we will also treat the animal with 2.0 mL of 10 mmol/L EF5 i.p three hours before sacrifice to enable later IHC stain for EF5.

IHC Staining: EF5 localizes to hypoxic tissue regions and has been used extensively for labeling of hypoxia in both animal and tumors. After administration to the animal, it is detected by monoclonal antibodies. The tissue sections are fixed in acetone for 10 minutes. Sections are then washed in PBS and blocked with a protein-blocking reagent (ID Labs, Inc., London, Ontario, Canada) for 15 minutes to prevent nonspecific antibody binding. They are stained with a cyanine-5-conjugated mouse anti-EF5 (1/50) antibody for 1 hour in a humidified chamber (antibody dilutions indicated in parentheses). Finally, sections are washed in PBS for two-photon fluorescent imaging. Cy5 fluorescence, representing hypoxic regions will be imaged with 665 to 695 nm emission filters.

Second Harmonic Generation (SHG) Imaging of Collagen: A key strength of multiphoton imaging is the ability to image elastin and collagen within a tissue without the need for exogenous labeling by exploiting the SHG signal that is generated from the laser excitation. SHG is a scattering process and therefore emits light at exactly half the excitation wavelength. A narrow band reflection filter extracts the SHG signal clearly from the remaining signals. Of particular note with regards to this method, the system has the ability to image collagen remodeling in the vascular tissue in response to angiogenesis, and collagen can be imaged in a mouse infarct in backscatter mode. The changes in the heart function in response to increased collagen deposition can have clinically important ramifications. This is the first assay method to provide information about this critical aspect of angiogenesis and ischemia at the microscopic 3D level.

To perform this measurement, two treated and two control rabbits at each time point of day 2, 8 and 30 are used in the above procedure. The rabbit heart can be sectioned 8-10 mm from the apical end embedded in 7% agarose. Good results has been obtained with this concentration of agarose for vibratoming of rabbit heart sections of 100 microns which have been cast with PU4ii. The tissue block can be mounted on the 3D tissue cytometer and 3D images can be acquired according the procedure explained herein.

To demonstrate the ability to overlay IHC stained images onto the original data set, the system retrieves every tenth 100 µm thick section (total 6-8 sections) for IHC staining which has been transferred from the tissue with the tissue section retrieval module described herein. The system incorporates automated transfer of each section to an indexed eppendorf tubes. The position is logged with respect to the entire 3D stack, and IHC stained. Afterwards each individual capture slice is mounted and reimaged on the MMM system and the resulting images overlaid onto the originals.

As stated above, 5 components are examined:

TABLE B2

| Component | Label | Wavelength | Significance |
|---|---|---|---|
| Vasculature | PU4ii Casting | 600 | Angiogenic response |
| Collagen | SHG/intrinsic | 400 | Fibrosis/Infarct region |
| Nuclei | Intravital Hoescht 33342 | 480 | Tissue state/necrosis |
| EF5 | Injection followed by IHC | 650 | Tissue Hypoxia |
| Autofluorescence | Intrinsic | 430-650 | Tissue ultrastructure |

Figures 14A, 14B:
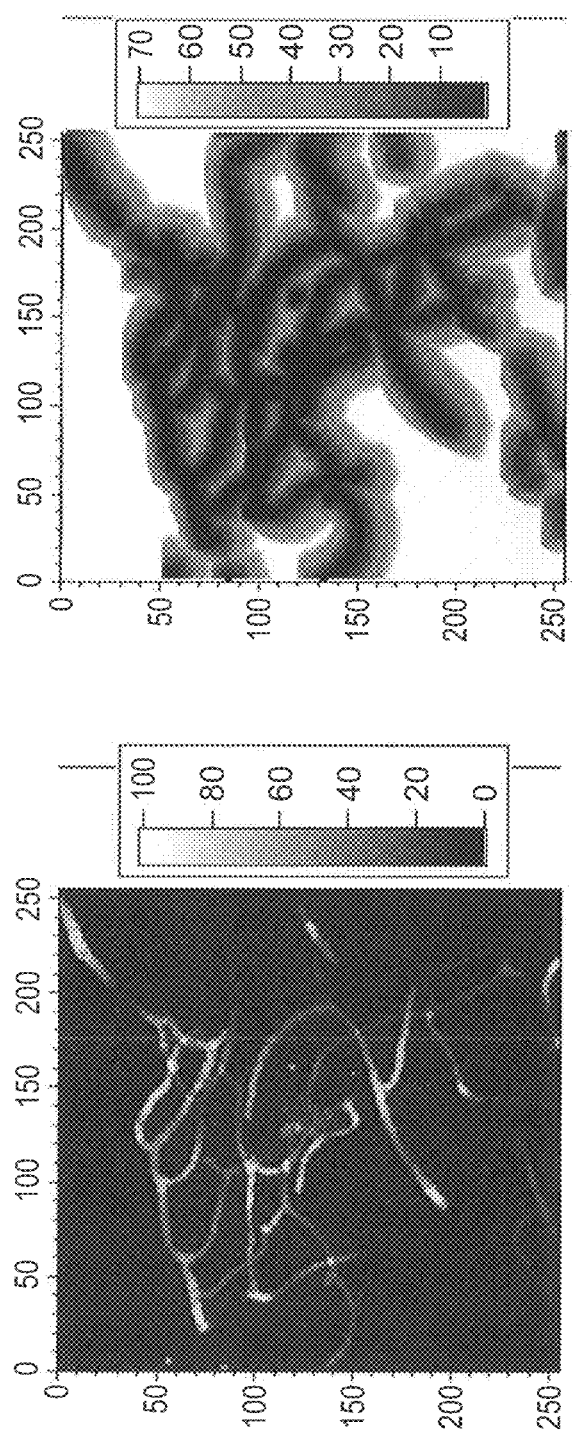
FIGS. 14A-14B are images of an animal brain cast and analysis.

3D Microvascular Density:

To confirm the changes observed previously in vascular density at various time points, calculate the distance to the nearest blood vessel to each point with a custom algorithm (as illustrated in FIGS. 14A and 14B). FIG. 14A shows the axial vessel orientation and FIG. 14B shows the lateral vessel orientation. A S/N ratio of 20-30 for the PU4ii cast make it possible to threshold and segment the vasculature without resorting to computationally intensive semi-manual algorithms. From this, the distance and geometry of tissue constituents such as cellular nuclei or collagen can easily be mapped with relation to the vasculature. The steps in the method are: 1. Intensity illumination correction; 2. Median filter noise reduction; 3. Thresholding; 4. Morphological closing to remove objects smaller than a few pixels; 5. 3D distance transform.

The present application has shown data for staining of the nuclei in mouse heart with intravital labeling using Hoescht 33342. The nuclei stained strongly and were straightforward to segment from the background heart tissue even in the presence of vascular staining and tissue autofluorescence. Additionally, using multiphoton tissue cytometry to conduct 3D image cytometric measurement on large populations of cells up to $10^5$ provides quantitative measurement on these cell populations within a 3D matrix. The cellular density can be calculated by segmenting the nuclei and then calculating the number of nuclei per unit volume as a function of position. The nuclei segmentation steps are 1. Automated threshold 2. Morphological opening/closing to remove spurious connections between nuclei 3. Morphological labeling to calculate nuclear volume and to assign an unique label to each nuclei candidate 4. Gating of nuclei targets that are outside the expected nuclear volume (500-3000 um$^3$).

Collagen content, hypoxia state and tissue ultrastructure can be identified spectrally and overlaid onto the segmented vascular images.

1. For the animals treated with bFGF, by calculating the average distance to the nearest blood vessel at each time point, demonstrate the vascular density trend displayed. One way ANOVA analysis of the mean distance can be used and a $P<0.05$ can be considered statistically significant.

2. For the untreated controls, the method demonstrates no increase in the vasculature density for Day 2 or Day 8 in comparison with Day 30. One way ANOVA analysis of the mean distance can be used and a $P<0.05$ can be considered statistically significant.

3. The system provides the average distance from the hypoxia border region to the vasculature for the treated animals and untreated controls.

4. To gauge tissue viability, the system calculates a correlation coefficient of the degree of overlap of the nuclei density and hypoxic regions. A student t-distribution and a $P<0.05$ can be considered significant.

An additional application is with regards to the production of brain atlases. Brain atlases are as essential for the research neuroscientist. Among the advantages of electronic atlases, compared with conventional paper atlases, are that an electronic atlas can contain images of all sections, allowing the brain to be "re-sectioned" in any desired plane, can offer multiple levels of resolution and a range of colors, can present structural features in 3D with variable transparency of surface and internal components and free rotation so as to optimize the user's view of structural relationships, can provide labels at the whim of the user in more than one language, is readily edited and updated, presents flexible indexing and ready access to other pertinent databases.

The complexity of the mammalian brain makes it necessary to rely on maps and atlases to analyze and interpret observations effectively. Modern neuroanatomic digital atlases are based on multiplemodality datasets that include histology, immunohistochemistry, magnetic resonance imaging, positron emission tomography and three-dimensional (3D) reconstruction to describe structures, nuclei and connectivity. With the advent of large-scale gene expression profiling using microarrays and high-throughput in situ hybridization in the present invention can build an anatomical brain atlas based on the transcriptome alone or using it as a key supporting modality. The brain exhibits complex and combinatorial gene expression patterns with variations depending on its highly differentiated structure. Expression patterns of individual genes in the cerebral cortex and other brain structures have been shown to highlight useful genetic markers for anatomic regions, boundaries, gradients and cell types. Profiling of larger brain structures using laser-capture microdissection and microarrays has suggested that gene expression patterns established during embryogenesis are largely retained in the adult and are important for regional specificity and for the functional connective relationships between brain regions. Combinatorial gene expression patterns have been found to define a diversity of neural progenitor domains that yield particular functional components in the mature brain. It follows that combinatorial gene expression characteristics should be reflected directly or indirectly in the neuroanatomic organization in the adult. Through the synthesis of in silico expression patterns across many genes in a spatially aligned dataset, an enhanced understanding of the relationships between genes expressed and structural and functional neuroanatomy may emerge.

Given the usefulness of brain atlases, there is a strong need for robust methods to quickly produce atlases of mouse brain for gene expression studies in automated manner. Unfortunately, the current method of employing serial section analysis is time consuming and labor intensive and often result in low quality datasets. However, using the whole mount tissue scanner method described herein, the present invention can quickly generate mouse brain atlases in an automated fashion.

Referring to the flowcharts in FIGS. 6-8, details of the steps involved in the entire process from mounting the mouse brain sample, imaging and sectioning, capturing of slices, processing of slices with more detailed analysis, re-imaging of the slices, and registration of slices back to the whole mount dataset.

Figure 15:
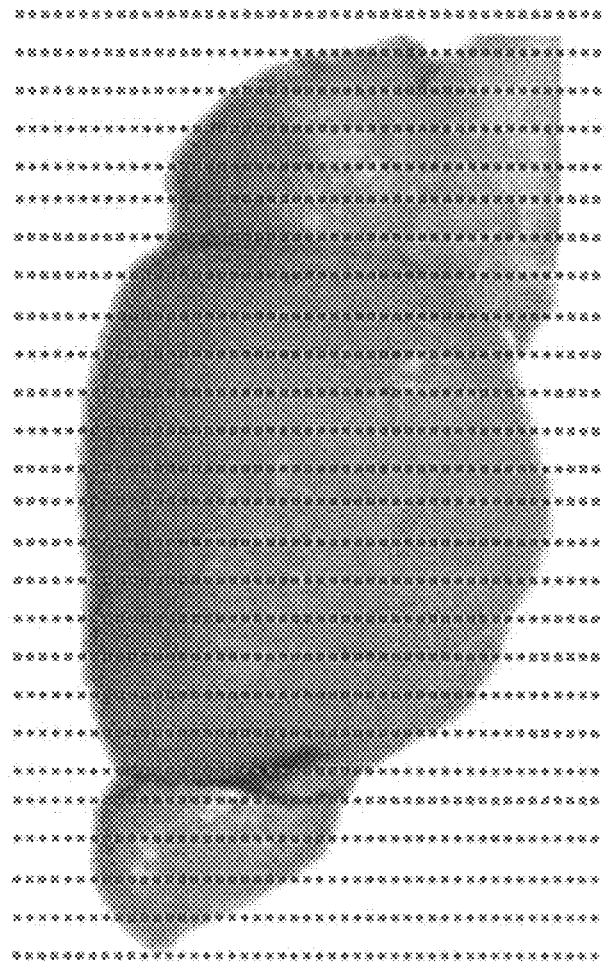
FIG. 15 illustrate a process for imaging, sectioning and analysis of an animal brain.
Figure 16A:
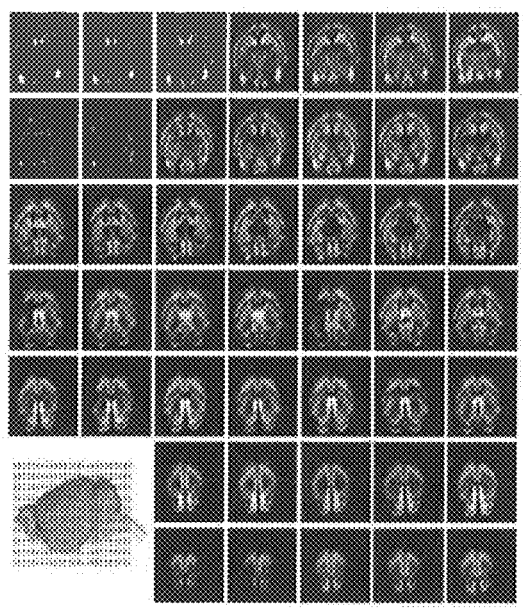
FIG. 16A-16D illustrate an animal brain atlas.
Figure 16B:
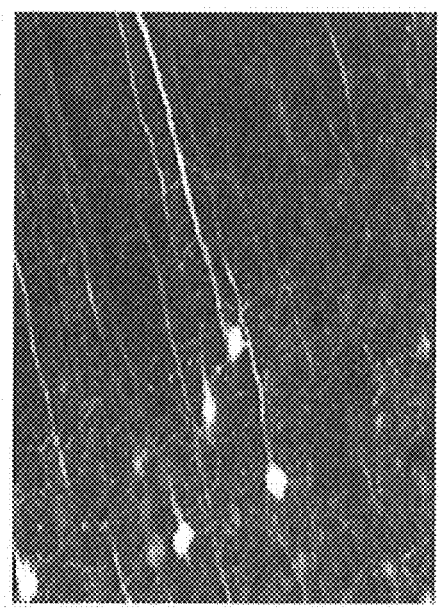
Figure 16C:
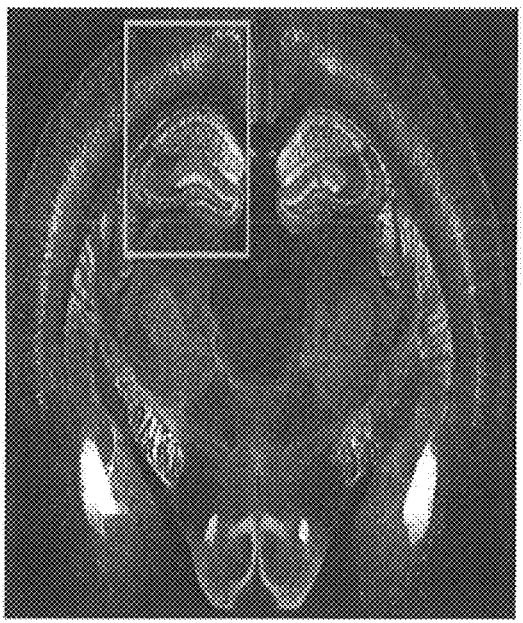
Figure 16D:
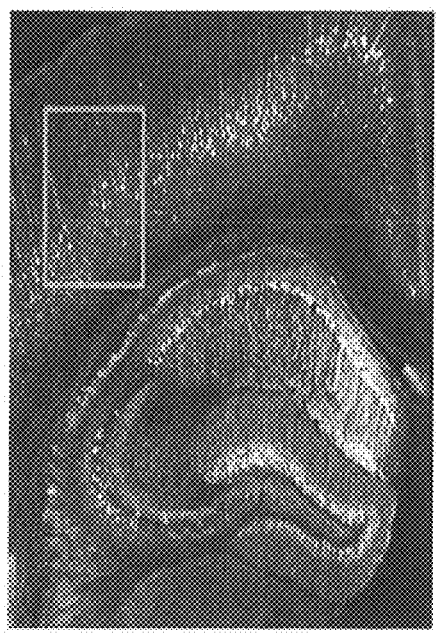
Figure 17A:
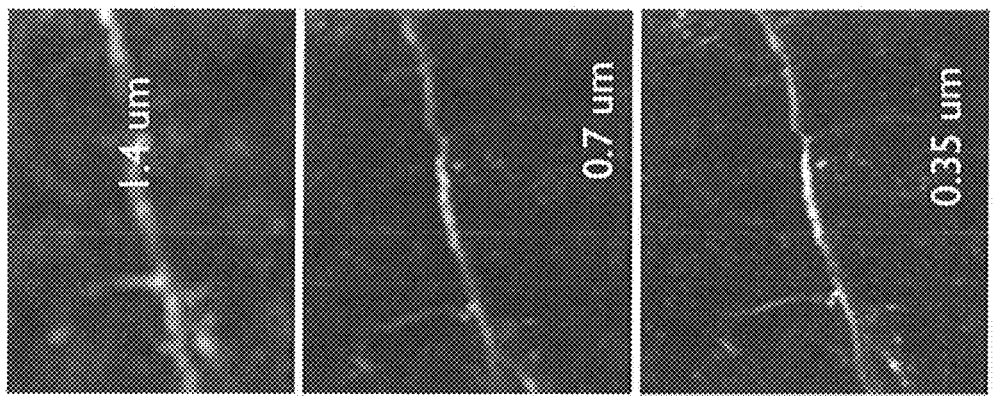
Figure 17A:

FIG. 15 is a diagram showing the general geometry of the alternation between optical imaging and a depth of, say, 50 µm, into the tissue, and mechanical sectioning, of say, 100 µm. Portions of a resulting dataset is shown in FIGS. 16A-16D.

The brain can be fixed with a perfusion fixation in a paraformaldehyde and then embedded into agarose block to improve mechanical stability during the sectioning process. The sample is mounted in a water bath to keep the tissue hydrated and to lubricate the cutting process by the vibratome. See FIG. 9 and the description thereof.

Figure 18:
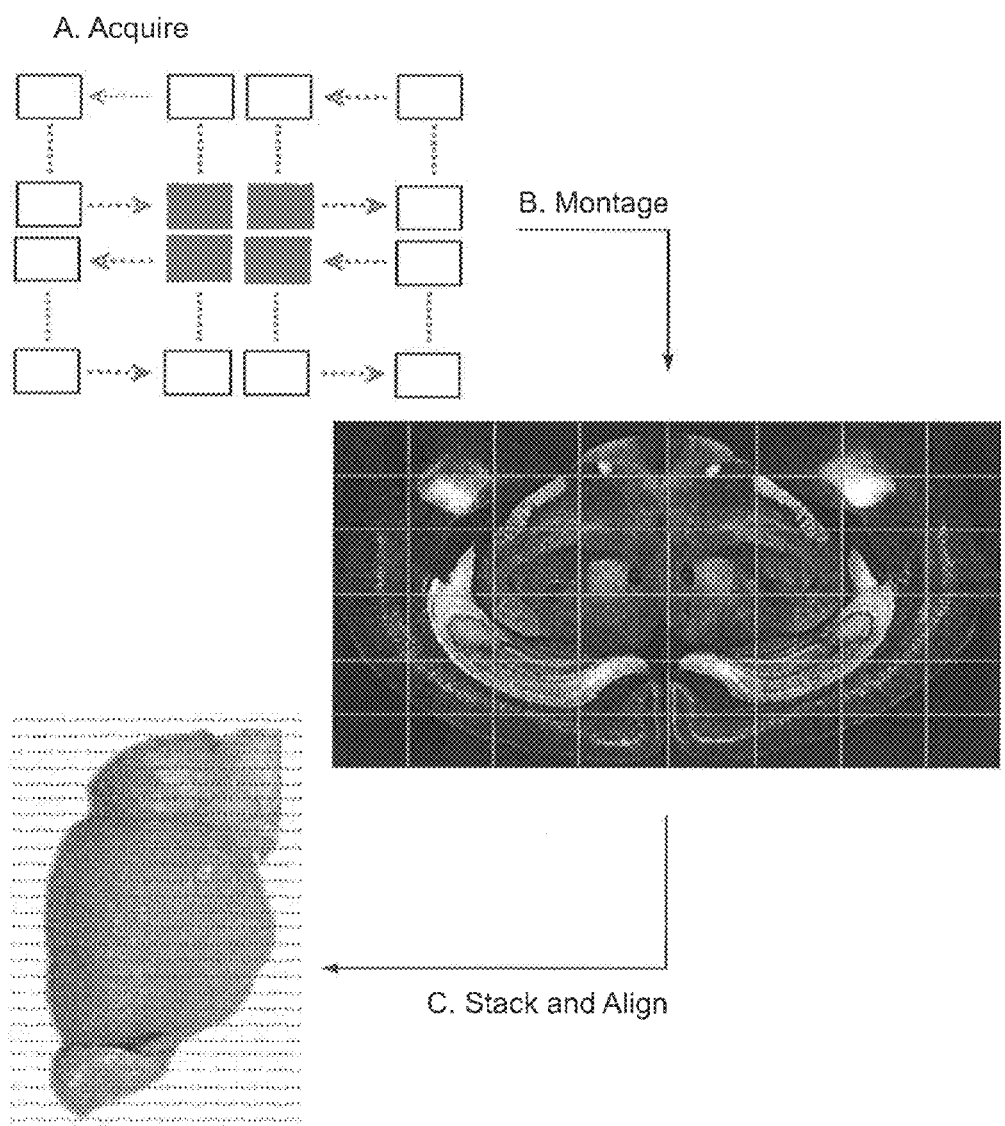
FIG. 18 illustrates imaging and alignment.

Mouse brain atlases with pixel samplings from 0.1 µm to 2.0 µm are possible to obtain with the optomechanics current implementation of this technique. Individual images with pixel dimensions of 416 to 2080 can be produced and physical dimensions from 200 µm to 2500 µm. See FIGS. 17A-17D. These individual images are filed and registered together to form a larger montage of a mouse brain sections. The sections can then be aligned with respect to one another to produce a mouse brain atlas. See FIG. 18.

Mechanical sections of 40 µm are greater is feasible. It is important to note that tissue sections on the size of 40 µm are near ideal for IHC studies. Optical section within the mechanical section on with z-spacing of 2 µm is also possible. Multichannel acquisition is also possible. To generate a brain atlas of 1.4 µm pixel sampling, at 100 micron coronal section interval, a time of 4 hours is required.

FIGS. 15 and 16A-16D show an example of the sort of datasets that can be generated with preferred embodiment of the invention.

Referring to FIG. 10 showing individual brain sections which have been captured and transferred to their own chamber in a well plate with an array 820 of single section chambers.

The next step after sectioning is to process each individual slice. As an example, we will use the IHC staining of each brain section as the processing example Immunocytochemistry comprises a number of methods, where antibodies are employed to localize antigens in tissues or cells for microscopic examination. There are several strategies to visualize the antibody. For transmitted light microscopy, color development substrates for enzymes are often used. The antibody can be directly labeled with the enzyme. However, such a covalent link between an antibody and an enzyme might result in a loss of both enzyme and antibody activity. For these reasons several multistep staining procedures have been developed, where intermediate link antibodies are used. In this protocol, we use the Vectastain ABC-kit. In the last staining step, the reaction is visualized with a 3-3' diaminobenzidine tetrahydrochloride (DAB).

There are several methods to IHC stain each brain section. The procedure involves free floating IHC staining of tissue sections as an example. An example free floating staining protocol can be found in Pete et al. 2002 part of which is below:

The free-floating sections were washed in phosphate-buffered saline (PBS) containing 0.3% Triton-X, and then 1-in-5 series of sections was xposed for 30 min to PBS-Triton solution containing 3% normal rabbit serum, to block nonspecific binding sites. After a further wash, the tissue was placed overnight at room temperature in a primary polyclonal antibody solution (1:10,000 dilution of rabbit anti-Fos in PBS; Oncogene). The sections were rinsed, incubated with biotinylated goat anti-rabbit secondary antiserum and further processed using the standard biotin avidin-peroxidase kit (Vector, ABC-elite kit). The immunoreaction was visualized by incubating the sections with 0.02% 3,3_-diaminobenzidine containing 0.01% hydrogen peroxide for 6 min A purple-black reaction product was obtained by adding nickel chloride to the peroxidase reaction (40_1 of 8% NiCl2 solution per 100 ml of DAB solution), as previously described (Haxhiu et al., 1996; Belegu et al., 1999, incorporated herein by reference). Subsequently, the sections were washed in PBS (2×), mounted on poly-L-lysine-coated slides, and prepared for in situ hybridization.

Once the brain tissue has been IHC stained, it can be reimaged by a variety of methods including wide field, multiphoton and confocal microscopy. Once reimaged, it can be registered and morphed onto the original dataset by a variety of registration and morphing algorithms. This process can be done manually or automatically by a computer. In this manner a 3D IHC stained dataset of mouse brain atlas can be produced.

While this invention has been particularly shown and described with reference to preferred embodiments thereof, it will be understood by those skilled in the art that various changes in form and details can be made without departing from the scope of the invention encompassed by the appended claims.

The invention claimed is:
1. A method of imaging tissue comprising:
illuminating a first region of the tissue with light;
detecting light from the tissue in response to the illuminating light to form at least a first image of the first region of the tissue wherein detected light includes light received from a depth in the tissue below a first sectioning depth to provide first registration data;
sectioning a portion of the tissue at the first sectioning depth to expose a second region of the tissue with a sectioning tool;
illuminating the second region of the tissue;
detecting light from the second region of the tissue to form at least a second image of the second region of the tissue;
sectioning at least a portion of the second region of the tissue with the sectioning tool at a second sectioning depth wherein detected light includes light received from a depth in the tissue below the second sectioning depth to provide second registration data;
processing the images of the first region of the tissue and the second region of the tissue including at least a first optical tomography image of the first region of the tissue and a second optical tomography image of the second region of the tissue; and
indexing the images using the first registration data and the second registration data to form a three dimensional image formed with at least the first optical tomography image of the first region of the tissue and the second optical tomography image of the second region of the tissue.

2. The method of claim 1 further comprising staining a first section of the tissue and a second section of the tissue.

3. The method of claim 2 wherein the staining step uses immunohistochemistry (IHC) staining.

4. The method of claim 1 further comprising processing the tissue with a process comprising one or more of staining analysis, mass spectrometry, micro dissection, and imaging mass spectrometry.

5. The method of claim 1 wherein the step of detecting light to form the image of the first region of the tissue further comprises imaging the first region of the tissue with a first imaging process.

6. The method of claim 5 further comprising imaging a first processed section of the tissue wherein said imaging of the first region of the tissue further comprises imaging with a second imaging process different from the first imaging process.

7. The method of claim 6 further comprising imaging the first region of the tissue with a two photon microscopy system.

8. The method of claim 6 further comprising imaging the first sectioned portion of the tissue with a confocal microscopy system.

9. The method of claim 6 wherein the illuminating steps comprise using a first excitation wavelength and a second excitation wavelength.

10. The method of claim 6 further comprising imaging a plurality of processed sections by detecting a different emission wavelength of light from each processed section.

11. The method of claim 1 wherein the tissue sample includes a vascular tissue such that vascular features of the image of the first region of the tissue are correlated with the vascular features of a processed tissue image.

12. The method of claim 1 wherein nuclei in the first image of the first region of tissue are correlated with the nuclei in a processed image of the first region of tissue.

13. The method of claim 1 wherein neurons are used to correlate a pre-sectioned region of the tissue with a post-sectioned region of the tissue.

14. The method of claim 1 further comprising using an anatomical structure in an image of a region of a brain to correlate different images of the region of the brain.

15. The method of claim 1 further comprising registering an image of a processed section of the tissue to a pre-sectioned image of the tissue.

16. The method of claim 1 further comprising imaging tissue including imaging an entire animal organ.

17. The method of claim 1 further comprising storing images for a brain atlas.

18. The method of claim 1 wherein the step of sectioning the tissue further comprises translating a sectioning tool to remove a section from the sample.

19. The method of claim 1 further comprising imaging processed sections by selecting an imaging modality comprising one or more of optical coherence tomography imaging (OCT), optical projection tomography imaging, confocal imaging, second harmonic generation imaging (SHG), wide field imaging and time resolved fluorescence imaging.

20. The method of claim 6 further comprising imaging a vascular cast.

21. A method of imaging brain tissue comprising:
illuminating a first region of the brain tissue with light;
detecting light from the brain tissue in response to the illuminating light to form at least a first image of the first region of the brain tissue;
sectioning a portion of the brain tissue to expose a second region of the brain tissue with a sectioning tool;
positioning the exposed second region of the brain tissue relative to a scanning lens using a translation stage connected to an automated control system;
illuminating the second region of the brain tissue;
detecting light from the second region of the tissue to form at least a second image of the second region of the tissue;
sectioning at least a portion of the second region of the brain tissue with the sectioning tool; and
processing the images of the first region of the brain tissue and the second region of the brain tissue including at least a first optical tomography image of the first region of the brain tissue and a second optical tomography image of the second region of the brain tissue with a data processor.

22. The method of claim 21 further comprising indexing the first optical tomography image to form a three dimensional optical tomography image.

23. The method of claim 21 wherein the sectioning tool comprises a microtome.

24. The method of claim 21 wherein the sectioning tool comprises a vibratome.

25. The method of claim 21 further comprising processing image data with a data processor that processes image data of a first sectioned tissue surface to correlate features of the first sectioned tissue surface with features of a second tissue surface that has been separated from.

26. The method of claim 21 further comprising stacking and aligning the images to form a three dimensional (3D) image.

27. The method of claim 21 further comprising registering images using vascular features within the images.

* * * * *